(12) United States Patent
Dimmeler et al.

(10) Patent No.: US 8,871,731 B2
(45) Date of Patent: Oct. 28, 2014

(54) MICRO-RNA FOR THE REGULATION OF CARDIAC APOPTOSIS AND CONTRACTILE FUNCTION

(75) Inventors: Stefanie Dimmeler, Frankfurt (DE);
Reinier A. Boon, Frankfurt (DE);
Ariane Fischer, Frankfurt (DE);
Andreas M. Zeiher, Frankfurt (DE)

(73) Assignee: Migagen Therapeutics, Inc., Boulder, CO (US)

( * ) Notice: Subject to any disclaimer, the term of this patent is extended or adjusted under 35 U.S.C. 154(b) by 0 days.

(21) Appl. No.: 13/422,932

(22) Filed: Mar. 16, 2012

(65) Prior Publication Data
US 2012/0238619 A1    Sep. 20, 2012

Related U.S. Application Data

(60) Provisional application No. 61/453,391, filed on Mar. 16, 2011.

(51) Int. Cl.
*C12N 15/11*   (2006.01)
*A61K 31/7125* (2006.01)
*C12N 15/113*  (2010.01)
*A61K 31/712*  (2006.01)

(52) U.S. Cl.
CPC ............ *A61K 31/712* (2013.01); *A61K 31/7125* (2013.01); *C12N 2310/113* (2013.01); *C12N 15/113* (2013.01)
USPC ..................................................... 514/44 A

(58) Field of Classification Search
USPC ..................................................... 514/44 A
See application file for complete search history.

(56) References Cited

U.S. PATENT DOCUMENTS

| | | | |
|---|---|---|---|
| 2005/0182005 A1* | 8/2005 | Tuschl et al. | 514/44 |
| 2009/0227533 A1 | 9/2009 | Bader et al. | |
| 2010/0310504 A1 | 12/2010 | Lowe et al. | |
| 2012/0165392 A1 | 6/2012 | Olson et al. | |
| 2013/0005658 A1* | 1/2013 | Olson et al. | 514/16.4 |

FOREIGN PATENT DOCUMENTS

| | | |
|---|---|---|
| WO | WO2010/135570 A1 * | 11/2010 |
| WO | WO 2011/084460 A1 | 7/2011 |

OTHER PUBLICATIONS

Fellmann et al. Mol. Cell 2011, 41:733-746.*
Lin et al. Arterioscler Thromb Vasc Biol. 2010;30:724-732, pp. 1-63.*
Bernardo et al. (PNAS 2012. 109: 17615-20, pp. 1-6).*
Small et al. Nature 469, 2011, pp. 336-342.*
Boon et al., Abstract 14023: Inhibition of the Age-induced microRNA-34 Improves Recovery After AMI in Mice, Circulation. 2010;122:A14023.
Khanna et al., Abstract 2423: Microrna-34 Cluster Regulates Cardiac Fibroblast Differentiation: Significance in Fibrosis of the Ischemia-Reperfused Heart. Circulation. 2009;120:S634-S635.
Thygesen et al., Third Universal Definition of Myocardial Infarction, Journal of the American College of Cardiology. 2012;60(16):1581-98.

* cited by examiner

*Primary Examiner* — Brian Whiteman
(74) *Attorney, Agent, or Firm* — Cooley LLP

(57) ABSTRACT

The present invention relates to treating or preventing age-related cardiomyopathy by modulating the expression or activity of a miR-34 family member and/or PNUTS. Methods of treating or preventing age-related cardiomyopathy include administering an inhibitor of miR-34 expression or activity or an agonist of PNUTS expression or activity. Also provided herein are methods of treating or preventing cardiac fibrosis and myocardial infarction by administering an inhibitor of miR-34 expression or activity or an agonist of PNUTS expression or activity.

17 Claims, 15 Drawing Sheets

FIGURE 1D-1F
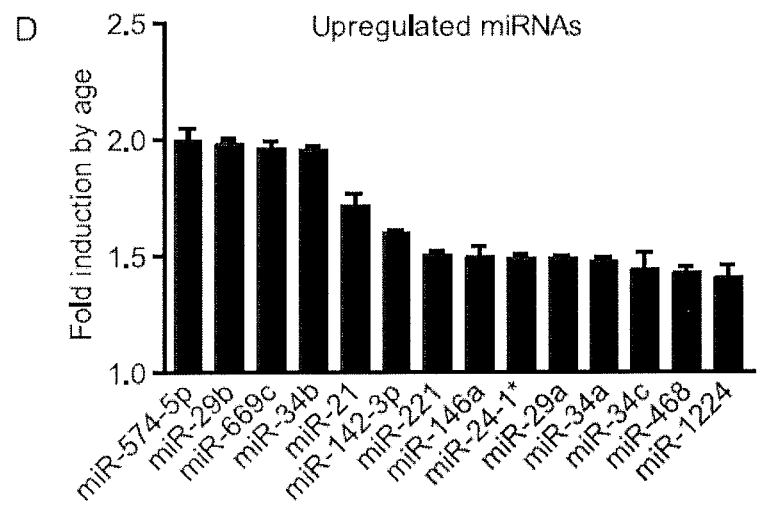
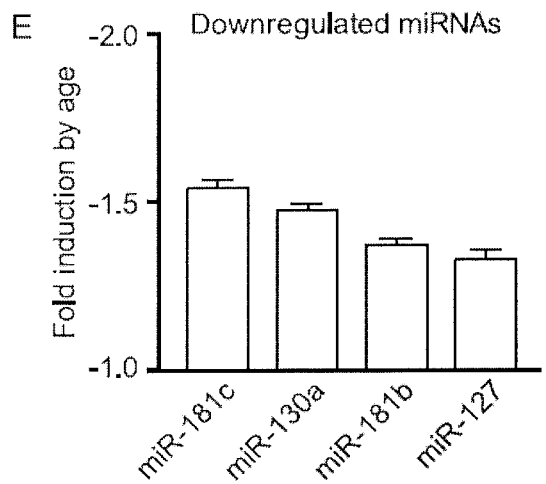
F    Genomic Organization of miR-34
pri-miR-34a:
───────── miR-34a ───────── Chr. 4
pri-miR-34b/34c:
───── miR-34b ── miR-34c ── Chr. 9
miR-34a:  UGGCAGUGUCUUAGCUGGUUGU
miR-34b: UAGGCAGUGUCAUUAGCUGAUUG
miR-34c:  AGGCAGUGUAGUUAGCUGAUUGC

MICRO-RNA FOR THE REGULATION OF CARDIAC APOPTOSIS AND CONTRACTILE FUNCTION

CROSS-REFERENCE TO RELATED APPLICATIONS

This application claims priority to U.S. Provisional Application Ser. No. 61/453,391, filed Mar. 16, 2011, which is herein incorporated by reference in its entirety.

DESCRIPTION OF THE TEXT FILE SUBMITTED ELECTRONICALLY

The contents of the text file submitted electronically are incorporated herein by reference in their entirety: A computer readable format copy of the Sequence Listing (filename: MIRG-027-01US_ST25.txt, date recorded: Mar. 16, 2012, file size 20 kilobytes).

FIELD OF THE PRESENT INVENTION

The present invention relates generally to the field of aging, cardiology, pathology and molecular biology. In particular, the present invention relates to the treatment and prevention of a cardiac disorder by administering an agent that modulates the activity or expression of a microRNA (miRNA). The present invention encompasses a method of treating or preventing age-related cardiomyopathy, cardiac fibrosis and myocardial infarction by inhibiting the expression or activity of at least one miR-34 family member and/or enhancing the expression or activity of PNUTS.

BACKGROUND OF THE PRESENT INVENTION

Heart disease and its manifestations, including coronary artery disease, myocardial infarction, congestive heart failure and cardiac hypertrophy, clearly present a major health risk in the United States today. The cost to diagnose, treat and support patients suffering from these diseases is well into the billions of dollars. One particularly severe manifestation of heart disease is myocardial infarction.

Myocardial infarction, commonly known as a heart attack, is caused by a sudden and sustained lack of blood flow to the heart tissue, which is usually the result of a narrowing or occlusion of a coronary artery. Without adequate blood supply, the tissue becomes ischemic, leading to the death of cardiomyocytes (e.g. heart muscle cells) and vascular structures. The necrotic tissue resulting from the death of the cardiomyocytes is generally replaced by scar tissue, which is not contractile, fails to contribute to cardiac function, and often plays a detrimental role in heart function by expanding during cardiac contraction, or by increasing the size and effective radius of the ventricle, for example, becoming hypertrophic.

Recently, key roles of microRNAs in heart failure have been described, pointing to a new mode of regulation of cardiac disease. MicroRNAs (miRNAs) are small, non-protein coding RNAs of about 18 to about 25 nucleotides in length that are derived from individual miRNA genes, from introns of protein coding genes, or from poly-cistronic transcripts that often encode multiple, closely related miRNAs. See review by Carrington et al. (*Science*, Vol. 301(5631):336-338, 2003). MiRNAs act as repressors of target mRNAs by promoting their degradation, when their sequences are perfectly complementary, or by inhibiting translation, when their sequences contain mismatches.

MiRNAs are transcribed by RNA polymerase II (pol II) or RNA polymerase III (pol III; see Qi et al. (2006) *Cellular & Molecular Immunology*, Vol. 3:411-419) and arise from initial transcripts, termed primary miRNA transcripts (pri-miR-NAs), that are generally several thousand bases long. Pri-miRNAs are processed in the nucleus by the RNase Drosha into about 70- to about 100-nucleotide hairpin-shaped precursors (pre-miRNAs). Following transport to the cytoplasm, the hairpin pre-miRNA is further processed by Dicer to produce a double-stranded miRNA. The mature miRNA strand is then incorporated into the RNA-induced silencing complex (RISC), where it associates with its target mRNAs by base-pair complementarity. In the relatively rare cases in which a miRNA base pairs perfectly with an mRNA target, it promotes mRNA degradation. More commonly, miRNAs form imperfect heteroduplexes with target mRNAs, affecting either mRNA stability or inhibiting mRNA translation.

Recently, signature expression patterns of miRNAs associated with pathological cardiac hypertrophy, heart failure and myocardial infarction in humans and mouse models of heart disease have been identified (van Rooij et al (2006) Proc. Natl. Acad. Sci., Vol. 103(48):18255-60; van Rooij et al., (2007) *Science*, Vol. 316: 575-579). Gain- and loss-of-function studies in mice have revealed profound and unexpected functions for these miRNAs in numerous facets of cardiac biology, including the control of myocyte growth, contractility, energy metabolism, fibrosis, and angiogenesis, providing glimpses of new regulatory mechanisms and potential therapeutic targets for heart disease. Remarkably, knock-out mice lacking disease-inducing miRNAs are normal, but display aberrant responses to cardiac stress, suggesting the dedication of these miRNAs to disease-related processes rather than tissue homeostasis, and pointing to their potential as therapeutic targets. Thus, miRNAs represent potential novel therapeutic targets for the development of treatments for a variety of diseases, including cardiovascular diseases, obesity, diabetes, and other metabolic disorders.

Aging is associated with impaired cardiac function (1), however, though miRNAs have recently emerged as key regulators of cardiovascular function (3, 4), miRNAs have thus far not been implicated in aging of the heart. Thus, identification and characterization of miRNAs dysregulated in the heart during aging, as well as the targets of the miRNAs, is important for the development of novel therapeutic approaches for the treatment of age-related cardiomyopathies, and cardiovascular diseases, such as myocardial infarction.

SUMMARY OF THE PRESENT INVENTION

The present invention is based, in part, on the discovery that dysregulation of miRNAs in the cardiac tissue during aging contributes to the adverse effects of aging on the heart, such as the development cardiovascular diseases. Modulation of these identified miRNAs presents a novel therapeutic approach for treating or preventing cardiovascular diseases, such as myocardial infarction.

Accordingly, the present invention provides a method of treating or preventing age-related cardiomyopathy in a subject in need thereof comprising administering to the subject an inhibitor of at least one miR-34 family member and/or an agonist of PNUTS. Also provided herein is a method of treating or preventing cardiac fibrosis or myocardial infarction in a subject in need thereof comprising administering to the subject an inhibitor of at least one miR-34 family member and/or an agonist of PNUTS. The present invention also encompasses a method of regulating apoptosis of cardiomyocytes and contractile function in a subject in need thereof comprising administering to the subject an inhibitor of at least one miR-34 family member and/or an agonist of PNUTS. The miR-34 family member can be miR-34a, miR-34b, miR-34c or combinations thereof.

The inhibitor of miR-34 can be an antagomir, an antisense oligonucleotide, or an inhibitory RNA molecule. In one embodiment, the inhibitor of a miR-34 family member is an antisense oligonucleotide having a sequence that is at least partially complementary to a mature miR-34a sequence. The antisense oligonucleotide can comprise a sequence that is at least partially complementary to a sequence of 5'-UG-GCAGUGUCUUAGCUGGUUGU-3' (SEQ ID NO: 1). The antisense oligonucleotide can comprise at least one sugar and/or backbone modification. The sugar modification can be a 2'-O-alkyl modification or a bicyclic sugar nucleoside modification. In one embodiment, the bicyclic sugar nucleoside modification is a locked nucleic acid (LNA). The backbone modification can be a phosphorothioate linkage. The antisense oligonucleotide can be about 8 to about 18 nucleotides or about 12 to about 16 nucleotides in length.

The present invention also provides that the inhibitor can be administered to the subject by an intravenous or subcutaneous route of administration.

In some embodiments, apoptosis of cardiomyocytes and/or cardiac fibrosis is reduced in the subject following administration of the inhibitor as compared to an untreated subject. In yet another embodiment, contractile function is increased in the subject following administration of the inhibitor as compared to an untreated subject. In one embodiment, the expression of PNUTS is increased in the subject following administration of the inhibitor as compared to an untreated subject. The subject can be a human.

In some embodiments, the method may further comprise administering to the subject a second myocardial infarction therapy, such as a β blocker, an ionotrope, a diuretic, ACE-I, AII antagonist, BNP, a $Ca^{++}$-blocker, an endothelin receptor antagonist, or an HDAC inhibitor. The second therapy may be administered at the same time as, before, or after the miR-34 inhibitor or PNUTS agonist.

The present invention also encompasses pharmaceutical compositions comprising the miR-34 inhibitors described herein and a pharmaceutically acceptable carrier. In one embodiment, the pharmaceutical composition comprises an inhibitor of miR-34 and a pharmaceutically acceptable carrier, wherein the inhibitor is an antagomir, an antisense oligonucleotide, or an inhibitory RNA molecule. The pharmaceutical composition can also further comprise a second myocardial infarction therapy.

BRIEF DESCRIPTION OF THE DRAWINGS

FIG. 6. Proposed mechanism of miR-34a.

DETAILED DESCRIPTION OF THE INVENTION

Figure 1:
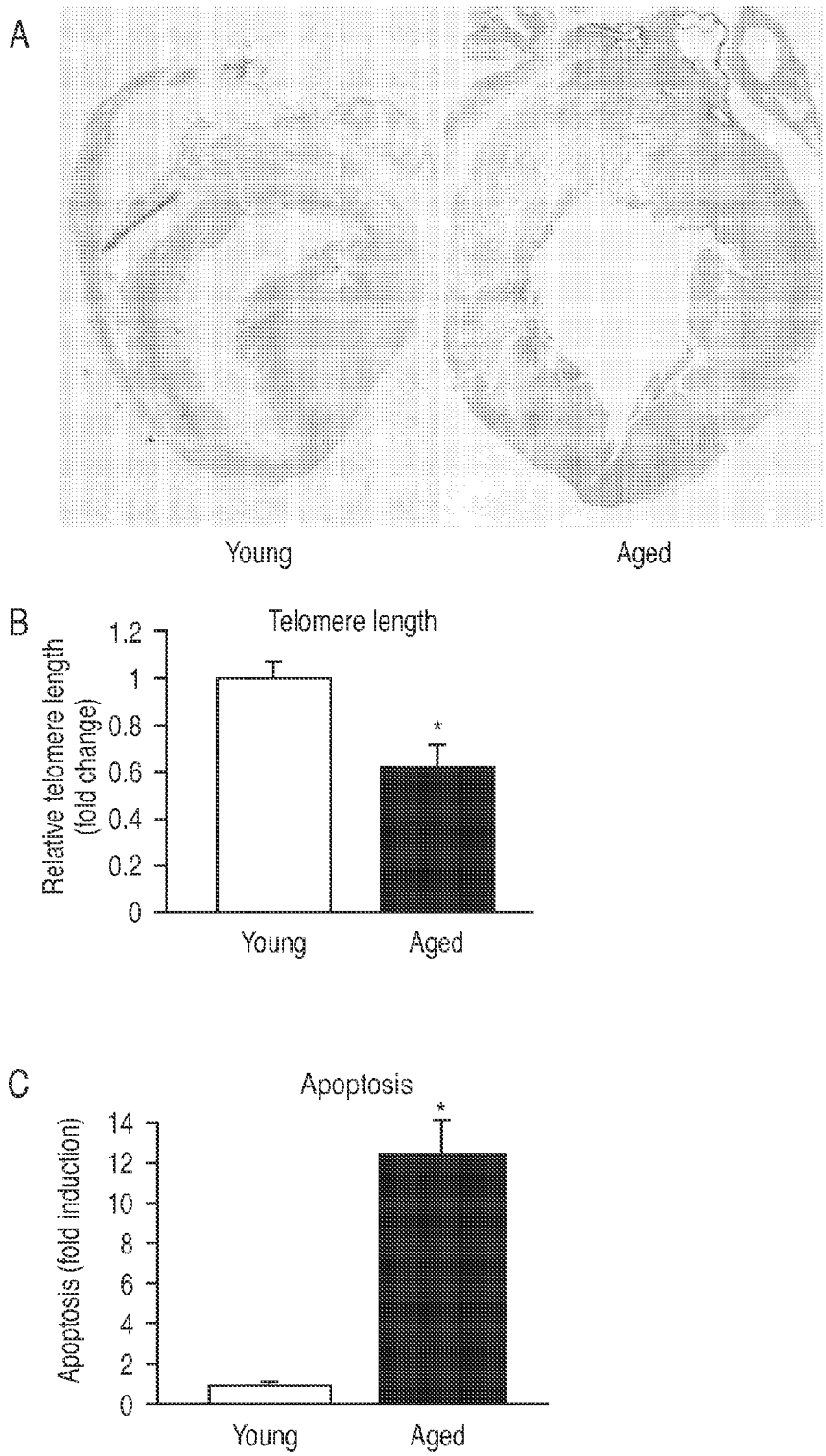
FIG. 1. Aging induces miR-34 expression in the mouse heart. (A) Hearts were harvested from young (6 weeks old, n=4) and aged (18 months old, n=4) C57/B16 mice and fibrosis was analyzed using Sirius red staining on histological sections. (B, C) DNA from young and aged hearts was subjected to real-time PCR-based telomere length measurement (B) and apoptosis was quantified on histological sections using TUNEL staining and confocal microscopy (C). (D, E) Summary of micro-array profiling results of miRNAs that are regulated by age in the heart; fold induction by age (array intensity of miRNA in aged hearts/miRNA in young hearts) is visualized for age-mediated upregulated (D) and downregulated (E) miRNAs. (F) Schematic representation of the primary transcripts encoding miR-34a (SEQ ID NO: 1), b (SEQ ID NO: 4), c (SEQ ID NO: 7) and their chromosomal location and sequence homologies in mouse. (G) Aging does not alter the cellular composition of mice hearts; fold induction by age (array intensity of miRNA in aged hearts/miRNA in young hearts) is visualized for cardiac-enriched (black bars), endothelial-enriched (white bar) and smooth muscle-enriched (grey bars) miRNAs. (H) Real-time PCR expression analysis of miR-34a was performed on RNA from aged and young mice hearts. (I) Quantitative real-time PCR was performed for miR-34a, b and c on RNA isolated from total mouse heart. (J) Heart cell-types were separated using Langendorff-perfusion digestion and miR-34a levels were measured by real-time PCR. n.gtoreq.3 for all experiments, *p<0.05 #p=0.053. (K) miR-34a is expressed by multiple cell types in the heart; heart tissue of young mice was analyzed using in situ hybridization for miR-34a; miR-34a is visualized in red, endothelial cells in green (lectin staining) and nuclei in blue (Hoecht 33342).

The present invention is based, in part, on the discovery that dysregulation of miRNAs in the cardiac tissue during aging contributes to the adverse effects of aging on the heart. Aging is the pre-dominant risk factor for cardiovascular diseases, thus, modulation of these identified miRNAs presents a novel therapeutic approach for treating or preventing cardiovascular diseases, such as myocardial infarction. In particular, the present invention relates to the role of the miR-34 family in aged cardiac tissue and the related discovery of reduced apoptosis in the heart due to inhibition of miR-34, induction of miR-34 after acute myocardial infarction (AMI) and the improvement in contractile recovery and reduction in apoptosis and fibrosis from subsequent silencing of miR-34 after AMI. The present invention also identifies a novel miR-34 target, PNUTS, which is reduced in aging hearts.

Accordingly, the present invention provides a method of treating or preventing age-related cardiomyopathy in a subject in need thereof comprising administering to the subject an inhibitor of at least one miR-34 family member and/or an agonist of PNUTS. As used herein "age-related cardiomyopathy" refers to the deterioration of the myocardium or myocardial damage as a result of intrinsic mechanisms occurring as the organism ages. Also provided herein is a method of treating or preventing cardiac fibrosis or myocardial infarction in a subject in need thereof comprising administering to the subject an inhibitor of at least one miR-34 family member and/or an agonist of PNUTS. The present invention also encompasses a method of regulating apoptosis of cardiomyocytes and contractile function in a subject in need thereof comprising administering to the subject an inhibitor of at least one miR-34 family member and/or an agonist of PNUTS.

As used herein, the term "subject" or "patient" refers to any vertebrate including, without limitation, humans and other primates (e.g., chimpanzees and other apes and monkey species), farm animals (e.g., cattle, sheep, pigs, goats and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, and the like). In some embodiments, the subject is a mammal. In other embodiments, the subject is a human.

In one embodiment, the present invention provides a method of treating or preventing age-related cardiomyopathy, cardiac fibrosis, myocardial infarction or apoptosis of cardiomyocytes in a subject in need thereof comprising administering to the subject an inhibitor of a miR-34 family member, such as an inhibitor of miR-34a, miR-34b, miR-34c, or any combination thereof. In mammalians, the miR-34 family comprises three processed miRNAs that are encoded by two different genes: miR-34a is encoded by its own transcript from chromosome 1, whereas miR-34b and miR-34c share a common primary transcript from chromosome 11. The pre-miRNA sequence is processed into a mature-5p or -3p sequence, in which the -5p sequence is processed from the 5' arm of the stem loop structure and the -3p sequence is processed from the 3' arm of the stem loop structure. The pre-miRNA (e.g. stem-loop sequences) and mature sequences for human miR-34a, miR-34b, and miR-34c are given below:

Human mature miR-34a-5p:

(SEQ ID NO: 1)

5'-UGGCAGUGUCUUAGCUGGUUGU-3'

Human mature miR-34a-3p:

(SEQ ID NO: 2)

5'-CAAUCAGCAAGUAUACUGCCCU-3'

Human pre-miR-34a:

```
                                             (SEQ ID NO: 3)
5'-
GGCCAGCUGUGAGUGUUUCUUUGGCAGUGUCUUAGCUGGUUGUUGUGAGC
AAUAGUAAGGAAGCAAUCAGCAAGUAUACUGCCCUAGAAGUGCUGCACGU
UGUGGGGCCC-3'

Human mature miR-34b-5p:
                                             (SEQ ID NO: 4)
5'-UAGGCAGUGUCAUUAGCUGAUUG-3'

Human mature miR-34b-3p:
                                             (SEQ ID NO: 5)
5'-CAAUCAGCAAGUAUACUGCCCU-3'

Human pre-miR-34b:
                                             (SEQ ID NO: 6)
5'-
GUGCUCGGUUUGUAGGCAGUGUCAUUAGCUGAUUGUACUGUGGUGGUUAC
AAUCACUAACUCCACUGCCAUCAAAACAAGGCAC-3'

Human mature miR-34c-5p:
                                             (SEQ ID NO: 7)
5'-AGGCAGUGUAGUUAGCUGAUUGC-3'

Human mature miR-34c-3p:
                                             (SEQ ID NO: 8)
5'-AAUCACUAACCACACGGCCAGG-3'

Human pre-miR-34c:
                                             (SEQ ID NO: 9)
5'-
AGUCUAGUUACUAGGCAGUGUAGUUAGCUGAUUGCUAAUAGUACCAAUCA
CUAACCACACGGCCAGGUAAAAAGAUU-3'
```

It is understood that all ribonucleic acid sequences disclosed herein can be converted to deoxyribonucleic acid sequences by substituting a thymidine base for a uridine base in the sequence. Likewise, all deoxyribonucleic acid sequences disclosed herein can be converted to ribonucleic acid sequences by substituting a uridine base for a thymidine base in the sequence. Deoxyribonucleic acid sequences, ribonucleic acid sequences, and sequences containing mixtures of deoxyribonucleotides and ribonucleotides of all sequences disclosed herein are included in the invention.

In one embodiment, a method of treating or preventing age-related cardiomyopathy, cardiac fibrosis, myocardial infarction or apoptosis of cardiomyocytes in a subject in need thereof comprises administering to the subject an inhibitor of a miR-34 family member, such as an inhibitor of miR-34a, miR-34b, miR-34c, or any combination thereof. In one particular embodiment, the inhibitor is of miR-34a. In some embodiments, the inhibitor is an inhibitor of miR-34a-5p and/or miR-34a-3p. In some embodiments, the expression or activity of a miR-34 family member, such as miR-34a, miR-34b, miR-34c, or any combination thereof, is reduced in the heart cells of the subject following administration of the inhibitor. In one embodiment, the expression or activity of miR-34a is reduced. In some embodiments, the expression of miR-34a-5p and/or miR-34a-3p is reduced.

"Heart cells," as used herein, include cardiomyocytes, cardiac fibroblasts, and cardiac endothelial cells. In one particular embodiment, the expression or activity of a miR-34 family member, such as miR-34a, miR-34b, miR-34c, or any combination thereof, is reduced in cardiomyocytes of the subject following administration of the miR-34a, miR-34b, and/or miR-34c inhibitor. In one particular embodiment, the expression or activity of miR-34a is reduced in cardiomyocytes of the subject following administration of the miR-34a inhibitor. In other embodiments, the expression or activity of miR-34a-5p and/or miR-34a-3p is reduced in cardiomyocytes of the subject following administration of the miR-34a-5p and/or miR-34a-3p inhibitor. In another particular embodiment, the expression or activity of PNUTS is increased in cardiomyocytes of the subject following administration of the PNUTS agonist. In some embodiments, age-related cardiomyopathy is prevented or treated. In another embodiment, deterioration of the myocardium or myocardial damage due to aging is reduced. In yet another embodiment, apoptosis of cardiomyocytes or cardiac fibrosis is reduced. In still yet another embodiment, contractile function is increased.

In another embodiment, the present invention provides a method of treating or preventing age-related cardiomyopathy, cardiac fibrosis, myocardial infarction or apoptosis of cardiomyocytes in a subject in need thereof comprising administering to the subject an agonist of PNUTS (phosphatase nuclear targeting subunit, or phosphatase 1 nuclear targeting subunit), which has also been referred to as PPP1R10 (protein phosphatase 1, regulatory subunit 10). PNUTS is a 114 kDa protein. The mRNA and amino acid sequence of PNUTS are given below:

```
PNUTS mRNA Sequence (4540 bp) (SEQ ID NO: 10):
  1 ATTCTGGGGT TCGTTTAGAG GTTTGAATTT TCTCGGAGAA AGACAGGCCG GCCCCAGAGA
 61 AAACAGAAAC AAGCCGCAGC AACATCTAAG CCCTTGAAAG GATCCTGAGA GAGGGGGAA
121 AGGGAAAACA GCAGCCACCA GCCCAACCAC TTGTGTCTTC TGCCCCTTCC CACCTATCTT
181 GCCCACCCCA CCAGCCCACG CTGCTTGGGA CTTGAAATCT GTGGCCGAAG GACCGTCACT
241 ACATAACTTC AAAAATAATC AACCACCCTC CCTTCCCAAA CCACCCAAAT TCACTCATCC
301 AGCGTTTACT TTTTTGAATC CACTCAGAAC TTTTTTCTGC GACCCCCCTC CCTAAATGGA
361 GTTGGGTGGG GGGGAAATGA ATACTGAGTT GGCCTTTATT TTTTAAAAGA CTTTTTGATC
421 CAATGAGGCC CCCTAAATAA TTGAGTTTTG GGTCCTGGTT GGTTGTTTTA TTTTTTTTCC
481 TCCAAAATTT TACCCCCTCC CCCCTGAGCC CGAGGTGCTG ACGTCGCAAA AAAATTGGAT
541 AAAACCACCA TCATGGGTTC GGGTCCCATA GACCCCAAAG AACTTCTCAA GGGCCTGGAC
601 AGCTTCCTTA ACCGAGATGG GGAAGTCAAA AGTGTGGATG GGATTTCCAA GATCTTCAGT
```

```
-continued
 661 TTGATGAAGG AAGCACGAAA GATGGTGAGT CGATGCACTT ACTTGAACAT TCTCCTGCAG
 721 ACCCGTTCAC CAGAAATATT GGTCAAATTT ATTGACGTTG GCGGCTACAA ACTTCTTAAC
 781 AATTGGCTGA CGTATTCAAA GACAACCAAC AACATTCCCC TCCTCCAGCA AATTCTACTG
 841 ACCCTGCAGC ATCTACCGCT CACTGTAGAC CATCTCAAGC AGAACAACAC AGCTAAACTG
 901 GTGAAGCAGC TGAGCAAGTC AAGTGAGGAT GAAGAGCTCC GGAAATTGGC CTCAGTCCTT
 961 GTCAGCGACT GGATGGCTGT CATCCGCTCT CAGAGCAGTA CCCAGCCTGC TGAGAAAGAT
1021 AAGAAGAAAC GTAAAGATGA AGGAAAAAGT CGAACTACCC TTCCTGAGCG ACCTTTGACA
1081 GAGGTGAAGG CTGAGACCCG GGCTGAGGAG GCCCCAGAGA AGAAGAGGGA GAAGCCCAAG
1141 TCTCTTCGCA CCACAGCACC CAGTCATGCC AAGTTCCGTT CCACTGGACT AGAGCTGGAG
1201 ACACCATCCT TGGTGCCTGT GAAGAAGAAT GCCAGCACAG TGGTGGTTTC TGACAAGTAC
1261 AACCTTAAAC CCATCCCCCT CAAACGTCAG AGCAACGTAG CTGCTCCAGG AGATGCCACT
1321 CCCCCTGCAG AGAAGAAATA CAAGCCACTC AACACAACAC CTAATGCCAC CAAAGAGATC
1381 AAAGTGAAGA TCATCCCGCC ACAGCCTATG GAGGGCCTGG GCTTTCTGGA TGCTCTTAAT
1441 TCAGCCCCTG TTCCAGGCAT CAAAATTAAG AAGAAAAAAA AAGTACTGTC ACCTACGGCT
1501 GCCAAGCCAA GCCCCTTTGA AGGGAAAACG AGCACAGAAC CAAGCACAGC CAAACCTTCT
1561 TCCCCAGAAC CAGCACCACC TTCTGAGGCA ATGGACGCAG ACCGTCCAGG CACCCCGGTT
1621 CCCCCTGTTG AAGTCCCGGA GCTCATGGAT ACAGCCTCTT GGAGCCAGG AGCTCTGGAT
1681 GCCAAGCCAG TGGAGAGTCC TGGAGATCCT AACCAACTGA CCCGGAAAGG CAGGAAGAGG
1741 AAAAGTGTGA CATGGCCTGA GGAAGGCAAA CTGAGAGAAT ATTTCTATTT TGAATTGGAT
1801 GAAACTGAAC GAGTAAATGT GAATAAGATC AAGGACTTTG GTGAGGCGGC TAAGCGAGAG
1861 ATACTGTCAG ACCGACATGC ATTTGAGACA GCGCGGCGTC TGAGCCATGA TAACATGGAG
1921 GAGAAGGTGC CCTGGGTGTG CCCCCGGCCC CTGGTTCTGC CCTCACCTCT TGTCACCCCT
1981 GGAAGCAATA GTCAGGAGCG ATATATCCAG CTGAGCGGG AGAAGGGAAT CCTTCAGGAG
2041 CTCTTCCTGA CAAGGAGAG TCCTCATGAG CCTGATCCTG AGCCCTACGA GCCCATACCC
2101 CCTAAACTCA TCCCCCTGGA TGAGGAGTGT TCCATGGATG AGACTCCGTA TGTTGAGACT
2161 CTGGAACCTG GGGGGTCAGG TGGCTCACCT GATGGGGCAG GAGGCTCCAA GTTGCCTCCA
2221 GTTCTGGCCA ATCTTATGGG AAGCATGGGT GCTGGAAAGG GCCCCAAGG CCCTGGAGGA
2281 GGAGGCATTA ATGTCCAAGA GATCCTCACC TCCATCATGG GTAGCCCAAA CAGTCATCCT
2341 TCAGAGGAAC TACTGAAACA ACCAGACTAT TCGGACAAGA TCAAGCAGAT GCTGGTGCCA
2401 CATGGACTCC TAGGCCCTGG CCCAATAGCC AATGGTTTCC CACCAGGGGG TCCTGGGGGC
2461 CCCAAGGGCA TGCAGCACTT TCCCCCTGGA CCTGGGGGAC CTATGCCAGG TCCCCATGGA
2521 GGCCCTGGTG GGCCAGTGGG TCCACGTCTT CTGGGTCCTC CACCCCCTCC CCGGGGAGGT
2581 GATCCCTTCT GGGATGGCCC GGGCGACCCT ATGCGGGGTG GCCCAATGCG GGGGGGTCCA
2641 GGACCAGGTC CTGGACCATA CCATAGAGGC CGAGGTGGCC GAGGAGGAAA CGAACCTCCT
2701 CCTCCTCCTC CTCCATTCCG AGGCGCCAGA GGAGGTCGCT CTGGAGGAGG ACCCCCAAAT
2761 GGACGAGGGG CCCTGGTGG GGGCATGGTT GGAGGTGGTG GCATCGTCC TCACGAAGGC
2821 CCTGGTGGGG GCATGGGCAA CAGCAGTGGA CATCGTCCCC ACGAAGGCCC TGGCGGTGGC
2881 ATGGGAAGTG GGCATCGCCC CCATGAAGGC CTGGTGGTA GCATGGGTGG GGTGGAGGA
2941 CATCGTCCCC ACGAAGGCCC TGGCGGTGGC ATCAGTGGTG GCAGTGGCCA TCGTCCCCAT
3001 GAAGGCCCTG GCGGAGGAAT GGGTGCCGGT GGTGGACATC GCCCCACGA AGGCCCTGGC
3061 GGAAGCATGG GTGGAAGTGG TGGACATCGT CCCCATGAAG GCCCTGGACA CGGGGGGCCC
```

-continued

```
3121 CATGGCCACC GGCCTCATGA TGTCCCTGGT CACCGAGGCC ATGACCATCG AGGGCCGCCA
3181 CCTCATGAGC ACCGTGGCCA TGATGGTCCT GGCCACGGGG GAGGGGGCCA CCGAGGGCAC
3241 GATGGAGGCC ACAGCCATGG AGGAGACATG TCAAACCGCC CTGTCTGCCG ACATTTCATG
3301 ATGAAGGGCA ACTGCCGCTA TGAGAACAAC TGTGCCTTCT ACCACCCGGG TGTCAATGGG
3361 CCCCCCCTGC CCTAGGGACC ATTTGCCTGC CCTGTTCACA CAACCCCTGT GGACTGCAGC
3421 CTCGCTCTTT CCACCCTGTT ATGGCTTCTG TGAGGCCCAT TTTCCCTTTT CCCCAGCTGA
3481 TGAGGAGCCG GCCCCCTCAG TTCCCACTTG CTTGGGTTCC TGGGGGTTTT CTGATCACTG
3541 GTGCGCATTG ATGTACATAT TTTCCTCCAG TCTGGGGAGG AGAGAGACTG GAAACGTTCC
3601 TGGACTGCTG AAGAGGAGAC CCAGTTGGCT TCACTTTTTG AGAAGATTCG CCCTGTACCC
3661 CAAACCCCTT TCCAGTATTA CCCTTAATGC TTGAGAACCT AAAGCTGGTT ATCCTGGCGA
3721 ACACCCCTAC CCTTCTATTG CGGGTCCCCA CATGCACACA GAACTCTGAC ACAGGATCAG
3781 CTGCACTTAA GAAATCATCC CAGCTAAGTT CATTATTCCT CATGGGGTGG GGAGATGCTG
3841 AAAGGGGTAT TGTATATCCC ACTGCACTGA GAGGGCTCAA TCAGCTGGAT TTGAGTTCTG
3901 GAACACACAT CATCCCCACC CCTCCCCCAG CGTGGGCTCA CCATTCTTAG TCCTTTCTCA
3961 AGTGGGACCT TCAACTTTCT GTGAACACCC AGTCTGCGTC CTGGGTCTGC TAGGTTCGAT
4021 GATGGCGAAC TCGTATCTGC ATCCGGTGCA AGTTTTAGCT GGCAGAGGTG AGACCGGTGG
4081 TGCTGGTCTG CCTTTGCCAA CTATAGCCAG TCTGGAGACT TGATAAAATA CTTCAGTGAG
4141 ACCAGCTTCT CATCAACTTG GGCCCGGCGT GCTGGGCCTG AAAGTCACAC TACATGCACT
4201 GCCTTTGGGA GTCAGCTCAC TCCCTGCTCC CACCTGGAAC CTTGCCAGCG TGAAGGAGGC
4261 TTCCAGGTAC TTCACCCTGT CAACCACCTC TGAATCCCCA CCAGGCGCCT TCCTGGGTGG
4321 ATTCAACAAG ATGATTTTGC CCTTTCCCAG TTCTCTCCTT CACTTTGGCA TCAGTTGTTT
4381 TCTATGAAAA CAGTGGATTG GTTGGGTTTT GTGCAGGGTC TTGGGTTAGA GCCAAAATGG
4441 ATTTGAGGAT GAGTATTTTT TTTTTTGGTT TTGTATATTT TGTACATTAA TAATAAACAG
4501 TGGAAAGAGA AGCAGCTTAA AAAAAAAAAA AAAAAAAAA
```

PNUTS Amino Acid Sequence (940 aa) (SEQ ID NO: 11):

```
  1 MGSGPIDPKE LLKGLDSFLN RDGEVKSVDG ISKIFSLMKE ARKMVSRCTY LNILLQTRSP
 61 EILVKFIDVG GYKLLNNWLT YSKTTNNIPL LQQILLTLQH LPLTVDHLKQ NNTAKLVKQL
121 SKSSEDEELR KLASVLVSDW MAVIRSQSST QPAEKDKKKR KDEGKSRTTL PERPLTEVKA
181 ETRAEEAPEK KREKPKSLRT TAPSHAKFRS TGLELETPSL VPVKKNASTV VVSDKYNLKP
241 IPLKRQSNVA APGDATPPAE KKYKPLNTTP NATKEIKVKI IPPQPMEGLG FLDALNSAPV
301 PGIKIKKKKK VLSPTAAKPS PFEGKTSTEP STAKPSSPEP APPSEAMDAD RPGTPVPPVE
361 VPELMDTASL EPGALDAKPV ESPGDPNQLT RKGRKRKSVT WPEEGKLREY FYFELDETER
421 VNVNKIKDFG EAAKREILSD RHAFETARRL SHDNMEEKVP WVCPRPLVLP SPLVTPGSNS
481 QERYIQAERE KGILQELFLN KESPHEPDPE PYEPIPPKLI PLDEECSMDE TPYVETLEPG
541 GSGGSPDGAG GSKLPPVLAN LMGSMGAGKG PQGPGGGGIN VQEILTSIMG SPNSHPSEEL
601 LKQPDYSDKI KQMLVPHGLL GPGPIANGFP PGGPGGPKGM QHFPPGPGGP MPGPHGGPGG
661 PVGPRLLGPP PPPRGGDPFW DGPGDPMRGG PMRGGPGPGP GPYHRGRGGR GGNEPPPPPP
721 PFRGARGGRS GGGPPNGRGG PGGGMVGGGG HRPHEGPGGG MGNSSGHRPH EGPGGGMGSG
781 HRPHEGPGGS MGGGGHRPH EGPGGGISGG SGHRPHEGPG GGMGAGGGHR PHEGPGGSMG
841 GSGGHRPHEG PGHGGPHGHR PHDVPGHRGH DHRGPPPHEH RGHDGPGHGG GGHRGHDGGH
901 SHGGDMSNRP VCRHFMMKGN CRYENNCAFY HPGVNGPPLP
```

The agonist of PNUTS can be an agonist of PNUTS function, i.e. enhance the activity or expression of PNUTS. An agonist of PNUTS expression or activity can be a polynucleotide comprising a PNUTS sequence. For instance, in one embodiment the PNUTS agonist is a polynucleotide comprising a PNUTS nucleotide sequence (SEQ ID NO: 10), or functional fragment thereof. In another embodiment, the PNUTS agonist is a polynucleotide encoding a PNUTS amino acid sequence (SEQ ID NO: 11), or functional fragment thereof. In some embodiments, the expression or activity of PNUTS is increased in the heart cells of the subject following administration of the agonist. In one embodiment, the expression or activity of PNUTS is increased in cardiomyocytes following administration of the PNUTS agonist. In some embodiments, age-related cardiomyopathy is prevented or treated. In another embodiment, deterioration of the myocardium or myocardial damage due to aging is reduced. In yet another embodiment, apoptosis of cardiomyocytes or cardiac fibrosis is reduced following administration of the PNUTS agonist. In still yet another embodiment, contractile function is increased following administration of the PNUTS agonist.

In another embodiment, the subject in need thereof may be at risk for developing myocardial infarction. Such a subject may exhibit one or more risk factors including, but not limited to, long standing uncontrolled hypertension, pulmonary arterial hypertension, uncorrected valvular disease, chronic angina, recent myocardial infarction, congenital predisposition to heart disease or pathological hypertrophy. The subject at risk may be diagnosed as having a genetic predisposition to cardiac hypertrophy or may have a familial history of cardiac hypertrophy. In some embodiments, the subject at risk may be diagnosed with obesity, type II diabetes, hyperlipidemia, or metabolic syndrome.

Preferably, administration of an inhibitor of a miR-34 family member, such as an inhibitor of miR-34a, miR-34b, miR-34c, or any combination thereof, or an agonist of PNUTS to the subject results in the improvement of one or more symptoms of age-related cardiomyopathy in the subject. In another embodiment, administration of an inhibitor of a miR-34 family member, such as an inhibitor of miR-34a, miR-34b, miR-34c, or any combination thereof, or an agonist of PNUTS to the subject results in the improvement of one or more symptoms of myocardial infarction in the subject. In one embodiment, the inhibitor of miR-34 is of an inhibitor of miR-34a. In some embodiments, the inhibitor is an inhibitor of miR-34a-5p or miR-34a-3p.

The one or more improved symptoms may be, for example, increased exercise capacity, increased cardiac ejection volume, decreased left ventricular end diastolic pressure, decreased pulmonary capillary wedge pressure, increased cardiac output, increased cardiac index, lowered pulmonary artery pressures, decreased left ventricular end systolic and diastolic dimensions, decreased cardiac fibrosis, decreased collagen deposition in cardiac muscle, decreased left and right ventricular wall stress, decreased wall tension, increased quality of life, and decreased disease-related morbidity or mortality.

In one embodiment, inhibition of a miR-34 family member, such as miR-34a, miR-34b, miR-34c, or enhancement of PNUTS expression or activity of a subject suffering from myocardial infarction can reduce infarct size by decreasing the loss of heart cells (e.g. decreasing apoptosis of cardiomyocytes or apoptosis in the infarct zone). In one embodiment, the miR-34 family member is miR-34a. In another embodiment, the inhibition of miR-34a is of miR-34a-5p or miR-34a-3p.

In another embodiment, inhibition of a miR-34 family member, such as miR-34a, miR-34b, miR-34c, or enhancement of PNUTS expression or activity in the heart cells of a subject can reduce cardiac fibrosis. In one embodiment, the miR-34 family member is miR-34a. In another embodiment, the inhibition of miR-34a is of miR-34a-5p or miR-34a-3p.

In another embodiment, inhibition of a miR-34 family member, such as miR-34a, miR-34b, miR-34c, or enhancement of PNUTS expression or activity in the heart cells of a subject suffering from myocardial infarction can reduce fibrosis in the infarct zone. In one embodiment, the miR-34 family member is miR-34a. In another embodiment, the inhibition of miR-34a is of miR-34a-5p or miR-34a-3p.

In another embodiment, inhibition of a miR-34 family member, such as miR-34a, miR-34b, miR-34c, or enhancement of PNUTS expression or activity in the heart cells of a subject suffering from myocardial infarction improves contractile recovery. In one embodiment, the miR-34 family member is miR-34a. In another embodiment, the inhibition of miR-34a is of miR-34a-5p or miR-34a-3p.

In still another embodiment, cardiac function is stabilized in a subject suffering from myocardial infarction following inhibition of a miR-34 family member, such as miR-34a, miR-34b, miR-34c, or enhancement of PNUTS expression or activity in the heart cells of the subject. In one embodiment, the miR-34 family member is miR-34a. In another embodiment, the inhibition of miR-34a is of miR-34a-5p or miR-34a-3p.

In yet another embodiment, PNUTS is upregulated in the heart cells of a subject suffering from myocardial infarction following inhibition of a miR-34 family member, such as miR-34a, miR-34b, miR-34c in the heart cells of the subject. In one embodiment, the miR-34 family member is miR-34a. In another embodiment, the inhibition of miR-34a is of miR-34a-5p or miR-34a-3p. In yet another embodiment, PNUTS is upregulated in the heart cells of a subject suffering from myocardial infarction following enhancement of PNUTS expression.

In some embodiments, an inhibitor of a miR-34 family member is an antisense oligonucleotide. In one embodiment, the antisense oligonucleotide is to miR-34a, miR-34b, or miR-34c, such as to miR-34a-5p or miR-34a-3p. The antisense oligonucleotides can include ribonucleotides or deoxyribonucleotides or a combination thereof. Preferably, the antisense oligonucleotides have at least one chemical modification (e.g., sugar or backbone modification). For instance, suitable antisense oligonucleotides can be comprised of one or more "conformationally constrained" or bicyclic sugar nucleoside modifications (BSN) that confer enhanced thermal stability to complexes formed between the oligonucleotide containing BSN and their complementary microRNA target strand. For example, in one embodiment, the antisense oligonucleotides contain at least one "locked nucleic acid." Locked nucleic acids (LNAs) contain the 2'-O, 4'-C-methylene ribonucleoside (structure A) wherein the ribose sugar moiety is in a "locked" conformation. In another embodiment, the antisense oligonucleotides contain at least one 2', 4'-C-bridged 2' deoxyribonucleoside (CDNA, structure B). See, e.g., U.S. Pat. No. 6,403,566 and Wang et al. (1999) Bioorganic and Medicinal Chemistry Letters, Vol. 9: 1147-1150, both of which are herein incorporated by reference in their entireties. In yet another embodiment, the antisense oligonucleotides contain at least one modified nucleoside having the structure shown in structure C. The antisense oligonucleotides targeting a miR-34 family member, such as miR-34a, miR-34b, miR-34c, can contain combinations of BSN (LNA, CDNA and the like) or other modified nucleotides, and ribonucleotides or deoxyribonucleotides.

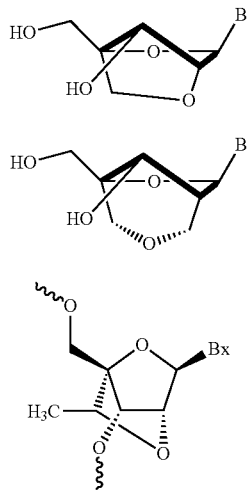

Alternatively, the antisense oligonucleotides can comprise peptide nucleic acids (PNAs), which contain a peptide-based backbone rather than a sugar-phosphate backbone. Other modified sugar or phosphodiester modifications to the antisense oligonucleotide are also contemplated. For instance, other chemical modifications that the antisense oligonucleotides can contain include, but are not limited to, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages (see, for example, U.S. Pat. Nos. 6,693,187 and 7,067,641, which are herein incorporated by reference in their entireties). In one embodiment, antisense oligonucleotides targeting a miR-34 family member, such as miR-34a, miR-34b, miR-34c, contain 2'O-methyl sugar modifications on each base and are linked by phosphorothioate linkages. Antisense oligonucleotides, particularly those of shorter lengths (e.g., less than 15 nucleotides) can comprise one or more affinity enhancing modifications, such as, but not limited to, LNAs, bicyclic nucleosides, phosphonoformates, 2' O-alkyl modifications and the like. In some embodiments, suitable antisense oligonucleotides are 2'-O-methoxyethyl "gapmers" which contain 2'-O-methoxyethyl-modified ribonucleotides on both 5' and 3' ends with at least ten deoxyribonucleotides in the center. These "gapmers" are capable of triggering RNase H-dependent degradation mechanisms of RNA targets. Other modifications of antisense oligonucleotides to enhance stability and improve efficacy, such as those described in U.S. Pat. No. 6,838,283, which is herein incorporated by reference in its entirety, are known in the art and are suitable for use in the methods of the invention. For instance, to facilitate in vivo delivery and stability, the antisense oligonucleotide can be linked to a steroid, such as cholesterol moiety, a vitamin, a fatty acid, a carbohydrate or glycoside, a peptide, or other small molecule ligand at its 3' end.

Preferable antisense oligonucleotides useful for inhibiting the activity of miRNAs are about 5 to about 25 nucleotides in length, about 10 to about 30 nucleotides in length, or about 20 to about 25 nucleotides in length. In certain embodiments, antisense oligonucleotides targeting miR-145 are about 8 to about 18 nucleotides in length, about 12 to about 16 nucleotides in length, about 10 to about 14 nucleotides in length, or about 11 to about 15 nucleotides in length. Any 7-mer, 8-mer or longer complementary to a miR-34 family member may be used, i.e., any antimiR complementary to the 5' end of the miRNA and progressing across the full or partial complementary sequence of the miRNA.

Antisense oligonucleotides can comprise a sequence that is at least partially complementary to a mature (-5p or 3p) miR-34 family member sequence, e.g. at least about 75%, 80%, 85%, 90%, 95%, 96%, 97%, 98%, or 99% complementary to a mature miR-34 family member sequence, such as miR-34a-5p or miR-34a-3p. In some embodiments, the antisense oligonucleotide can be substantially complementary to a mature miR-34 family member sequence such that the antisense oligonucleotide is at least about 90%, 95%, 96%, 97%, 98%, or 99% complementary to a target polynucleotide sequence, such as to miR-34a-5p or miR-34a-3p. In one embodiment, the antisense oligonucleotide comprises a sequence that is 100% complementary to a mature miR-34 family member sequence, such as to miR-34a-5p or miR-34a-3p. In certain embodiments, the antisense oligonucleotide is at least partially complementary to SEQ ID NO: 1 or 2. In other embodiments, the antisense oligonucleotide is at least partially complementary to SEQ ID NO: 4 or 5. In yet other embodiments, the antisense oligonucleotide is at least partially complementary to SEQ ID NO: 7 or 8.

For instance, in one embodiment, the antisense oligonucleotide is complementary to miR-34a-5p and has a sequence of 5'-ACAACCAGCUAAGACACUGCCA-3' (SEQ ID NO: 12) or a fragment thereof. In some embodiments, the antisense oligonucleotide has a sequence of 5'-CACUGCCA-3' (SEQ ID NO: 13) or 5'-ACACUGCC-3' (SEQ ID NO: 14). In another embodiment, the antisense oligonucleotide has a sequence of 5'-GACACUGCCA-3' (SEQ ID NO: 15) or 5'-AAGACACUGCCA-3' (SEQ ID NO: 16). In yet another embodiment, the antisense oligonucleotide has a sequence of 55'-CUAAGACACUGCCA-3' (SEQ ID NO: 17). In still another embodiment, the antisense oligonucleotide has a sequence of 5'-AGCUAAGACACUGCCA-3' (SEQ ID NO: 18) or 5'-CAGCUAAGACACUGCC-3' (SEQ ID NO: 19). In still another embodiment, the antisense oligonucleotide has a sequence of 5'-CCAGCUAAGACACUGCCA-3' (SEQ ID NO: 20). In certain embodiments, the antisense oligonucleotide has a sequence of 5'-AGCUAAGACACUGCC-3' (SEQ ID NO: 21).

In some embodiments, the antisense oligonucleotide is complementary to miR-34a-3p and has a sequence of 5'-AGGGCAGUAUACUUGCUGAUUG-3' (SEQ ID NO: 22) or a fragment thereof. Exemplary antisense oligonucleotides for inhibiting miR-34a-3p expression or activity include, but are not limited to, 5'-GCUGAUUG-3' (SEQ ID NO: 23), 5'-UGCUGAUU-3' (SEQ ID NO: 24), 5'-UUGCUGAUUG-3' (SEQ ID NO: 25), 5'-ACUUGCUGAUUG-3' (SEQ ID NO: 26), 5'-AUACUUGCUGAUUG-3' (SEQ ID NO: 27), 5'-GUAUACUUGCUGAUUG-3' (SEQ ID NO: 28), 5'-AGUAUACUUGCUGAUU-3' (SEQ ID NO: 29), 5'-CAGUAUACUUGCUGAUUG-3' (SEQ ID NO: 30), and 5'-GUAUACUUGCUGAUU-3' (SEQ ID NO: 31).

In one embodiment, the antisense oligonucleotide is fully phosphorothiolated. In another embodiment, the antisense oligonucleotide is partially phosphorothiolated. In some embodiments, the antisense oligonucleotide is a LNA antisense oligonucleotide or comprises a mixture of LNA and DNA. In yet another embodiment, the antisense oligonucleotide comprises a LNA and is fully phosphorothiolated. In one embodiment, the antisense oligonucleotide comprises the nucleotides sequence of SEQ ID NO: 12, 13, 14, 15, 16, 17, 18, 19, 20, 21, 22, 23, 24, 25, 26, 27, 28, 29, 30, or 31 is fully or partially phosphorothiolated and comprises a LNA.

In one embodiment, the antisense oligonucleotide targets base 2-17 of a mature miR-34 family member, such as SEQ ID NO: 19 for miR-34a-5p or SEQ ID NO: 29 for miR-34a-3p. In one embodiment, the antisense oligonucleotide that targets base 2-17 of a mature miR-34 family member is fully phosphorothiolated. In yet another embodiment, the antisense oligonucleotide that targets base 2-17 of a mature miR-34 family member is a mixture of LNA and DNA. In yet another embodiment, the antisense oligonucleotide that targets base 2-17 of a mature miR-34 family member is a LNA antisense oligonucleotide that is fully phosphorothiolated.

In some embodiments, the antisense oligonucleotides are antagomirs. "Antagomirs" are single-stranded, chemically-modified ribonucleotides that are at least partially complementary to a miR-34 family member sequence, such as to miR-34a-5p or miR-34a-3p. Antagomirs may comprise one or more modified nucleotides, such as 2'-O-methyl-sugar modifications. In some embodiments, antagomirs comprise only modified nucleotides. Antagomirs can also comprise one or more phosphorothioate linkages resulting in a partial or full phosphorothioate backbone. To facilitate in vivo delivery and stability, the antagomir can be linked to a cholesterol or other moiety at its 3' end. Antagomirs suitable for inhibiting a miR-34 family member can be about 15 to about 50 nucleotides in length, more preferably about 18 to about 30 nucleotides in length, and most preferably about 20 to about 25 nucleotides in length. The antagomirs can be at least about 75%, 80%, 85%, 90%, 95%, 96%, 97%, 98%, or 99% complementary to a mature miR-34 family member sequence, such as a -5p or -3p sequence. In some embodiments, the antagomir may be substantially complementary to a mature miR-34 family member sequence, that is at least about 95%, 96%, 97%, 98%, or 99% complementary to a target polynucleotide sequence. In other embodiments, the antagomirs are 100% complementary to a mature miR-34 family member sequence, such as to miR-34a-5p or miR-34a-3p. In one embodiment, the antagomir comprises the nucleotides sequence of SEQ ID NO: 12, 13, 14, 15, 16, 17, 18, 19, 20, 21, 22, 23, 24, 25, 26, 27, 28, 29, 30 or 31.

The inhibitory nucleotide molecules described herein preferably target the mature sequence of a miR-34 family member, such as miR-34a, miR34b, or miR-34c. In one embodiment, the inhibitor nucleotide molecules described herein target the mature sequence miR-34a. In one embodiment, the inhibitory nucleotide molecules described herein target the -5p sequence of miR-34a (SEQ ID NO: 1). In another embodiment, the inhibitory nucleotide molecules described herein target the -3p sequence of miR-34a (SEQ ID NO: 2). In some embodiments, inhibitors of miR-34a-5p and/or miR-34-3p are antagomirs comprising a sequence that is perfectly complementary to the miR-34a-5p or miR-34a-3p sequence. In one embodiment, an inhibitor of miR-34a-5p is an antagomir having a sequence that is partially or perfectly complementary to SEQ ID NO: 1. In another embodiment, an inhibitor of miR-34a-3p is an antagomir having a sequence that is partially or perfectly complementary to SEQ ID NO: 2. In some embodiments, inhibitors of miR-34a-5p and/or miR-34-3p are chemically-modified antisense oligonucleotides. In one embodiment, an inhibitor of miR-34a-5p is a chemically-modified antisense oligonucleotide comprising a sequence substantially complementary to SEQ ID NO: 1. In another embodiment, an inhibitor of miR-34a-3p is a chemically-modified antisense oligonucleotide comprising a sequence substantially complementary to 5'-SEQ ID NO: 2. As used herein "substantially complementary" refers to a sequence that is at least about 95%, 96%, 97%, 98%, 99%, or 100% complementary to a target polynucleotide sequence (e.g. mature, minor, or precursor miRNA sequence).

Antisense oligonucleotides or antagomirs may comprise a sequence that is substantially complementary to a precursor miRNA sequence (pre-miRNA) or primary miRNA sequence (pri-miRNA) for a miR-34 family member. In some embodiments, the antisense oligonucleotide comprises a sequence that is substantially complementary to a sequence located outside the stem-loop region of the pre-miR-34 family member sequence. In one embodiment, an inhibitor of miR-34 function is an antisense oligonucleotide having a sequence that is substantially complementary to a pre-miR-34 sequence, such as SEQ ID NO: 3, 6, or 9.

Any of the inhibitors or agonists described herein can be delivered to the target cell (e.g. heart) by delivering to the cell an expression vector encoding the miR-34 inhibitor or PNUTS agonist. A "vector" is a composition of matter which can be used to deliver a nucleic acid of interest to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, and the like. An expression construct can be replicated in a living cell, or it can be made synthetically. For purposes of this application, the terms "expression construct," "expression vector," and "vector," are used interchangeably to demonstrate the application of the invention in a general, illustrative sense, and are not intended to limit the invention.

In one embodiment, an expression vector for expressing an inhibitor of a miR-34 family member (such as miR-34a) comprises a promoter operably linked to a polynucleotide encoding an antisense oligonucleotide, wherein the sequence of the expressed antisense oligonucleotide is partially or perfectly complementary to a mature sequence of a miR-34 family member (e.g., SEQ ID NO: 1, 2, 4, 5, 7 or 8). In another embodiment, an expression vector for expressing a polynucleotide comprising a PNUTS sequence comprises a promoter operably linked to a polynucleotide comprising a PNUTS sequence (e.g., SEQ ID NO: 10). In yet another embodiment, an expression vector for expressing a protein sequence comprising a PNUTS sequence comprises a promoter operably linked to a polynucleotide encoding a PNUTS amino acid sequence of SEQ ID NO: 11. The phrase "operably linked" or "under transcriptional control" as used herein means that the promoter is in the correct location and orientation in relation to a polynucleotide to control the initiation of transcription by RNA polymerase and expression of the polynucleotide.

As used herein, a "promoter" refers to a DNA sequence recognized by the synthetic machinery of the cell, or introduced synthetic machinery, required to initiate the specific transcription of a gene. Suitable promoters include, but are not limited to RNA pol I, pol II, pol III, and viral promoters (e.g. human cytomegalovirus (CMV) immediate early gene promoter, the SV40 early promoter, and the Rous sarcoma virus long terminal repeat). In one embodiment, the promoter is a tissue-specific promoter. Of particular interest are muscle specific promoters, and more particularly, cardiac specific promoters. These include the myosin light chain-2 promoter (Franz et al. (1994) *Cardioscience*, Vol. 5(4):235-43; Kelly et al. (1995) *J. Cell Biol.*, Vol. 129(2):383-396), the alpha actin promoter (Moss et al. (1996) *Biol. Chem.*, Vol. 271(49): 31688-31694), the troponin 1 promoter (Bhavsar et al. (1996)

Genomics, Vol. 35(1):11-23); the Na+/Ca2+ exchanger promoter (Barnes et al. (1997) *J. Biol. Chem.*, Vol. 272(17): 11510-11517), the dystrophin promoter (Kimura et al. (1997) *Dev. Growth Differ.*, Vol. 39(3):257-265), the alpha7 integrin promoter (Ziober and Kramer (1996) *J. Bio. Chem.*, Vol. 271(37):22915-22), the brain natriuretic peptide promoter (LaPointe et al. (1996) *Hypertension*, Vol. 27(3 Pt 2):715-22) and the alpha B-crystallin/small heat shock protein promoter (Gopal-Srivastava (1995) *J. Mol. Cell. Biol.*, Vol. 15(12): 7081-7090), alpha myosin heavy chain promoter (Yamauchi-Takihara et al. (1989) *Proc. Natl. Acad. Sci. USA*, Vol. 86(10): 3504-3508) and the ANF promoter (LaPointe et al. (1988) *J. Biol. Chem.*, Vol. 263(19):9075-9078). In one embodiment, the tissue-specific promoter is an adipocyte-specific promoter, such as an adipocyte protein 2 (ap2)/fatty acid binding protein 4 (FABP4) promoter or a PPARγ promoter.

In certain embodiments, the promoter operably linked to a polynucleotide encoding an inhibitor to a miR-34 family member or an agonist of PNUTS (e.g. PNUTS sequence) can be an inducible promoter. Inducible promoters are known in the art and include, but are not limited to, tetracycline promoter, metallothionein IIA promoter, heat shock promoter, steroid/thyroid hormone/retinoic acid response elements, the adenovirus late promoter, and the inducible mouse mammary tumor virus LTR.

Methods of delivering expression constructs and nucleic acids to cells are known in the art and can include, for example, calcium phosphate co-precipitation, electroporation, microinjection, DEAE-dextran, lipofection, transfection employing polyamine transfection reagents, cell sonication, gene bombardment using high velocity microprojectiles, and receptor-mediated transfection.

The present invention also includes methods for scavenging or clearing inhibitors of a miR-34 family member following treatment. The method may comprise overexpressing binding sites for the inhibitors of the miR-34 family member in cardiac tissue. The binding site regions preferably contain a sequence of the seed region for the miR-34 family member. The seed region is the 5' portion of a miRNA spanning bases 2-8, which is important for target recognition. In some embodiments, the binding site may contain a sequence from the 3'UTR of one or more targets of the miR-34 family member, such as PNUTS, a target of miR-34a.

The present invention also includes pharmaceutical compositions comprising an inhibitor of a miR-34 family member, such as such as an inhibitor of miR-34a, miR-34b, miR-34c, or any combination thereof, and/or an agonist of PNUTS. Where clinical applications are contemplated, pharmaceutical compositions will be prepared in a form appropriate for the intended application. Generally, this will entail preparing compositions that are essentially free of pyrogens, as well as other impurities that could be harmful to humans or animals.

In one embodiment, the pharmaceutical composition comprises an effective dose of an inhibitor of a miR-34 family member, such as miR-34a, miR-34b, miR-34c, or any combination thereof, and/or an agonist of PNUTS, and a pharmaceutically acceptable carrier. For instance, the pharmaceutical composition comprises an effective dose of a modified antisense oligonucleotide targeting a miR-34 family member, such as miR-34a as described herein. In some embodiments, the pharmaceutical composition comprises a modified antisense oligonucleotide having a sequence selected from the group consisting of SEQ ID NO: 12, 13, 14, 15, 16, 17, 18, 19, 20, 21, 22, 23, 24, 25, 26, 27, 28, 29, 30 or 31. In some embodiments, the pharmaceutical composition comprises a modified antisense oligonucleotide having a sequence selected from the group consisting of SEQ ID NO: 12, 13, 14, 15, 16, 17, 18, 19, 20, 21, 22, 23, 24, 25, 26, 27, 28, 29, 30 or 31. In one embodiment, the pharmaceutical composition comprises an effective dose of an agonist of PNUTS, such as described herein. In some embodiments, the pharmaceutical composition comprises a nucleotide sequence of SEQ ID NO: 10, or a nucleotide sequence encoding an amino acid sequence of SEQ ID NO: 11, or a functional fragment thereof.

An "effective dose" is an amount sufficient to effect a beneficial or desired clinical result. An effective dose of a miRNA inhibitor or PNUTS agonist may be from about 1 mg/kg to about 100 mg/kg, about 2.5 mg/kg to about 50 mg/kg, or about 5 mg/kg to about 25 mg/kg. The precise determination of what would be considered an effective dose may be based on factors individual to each patient, including their size, age, type of disorder, and nature of inhibitor or agonist (e.g. antagomir, expression construct, antisense oligonucleotide, polynucleotide duplex, etc). Therefore, dosages can be readily ascertained by those of ordinary skill in the art from this disclosure and the knowledge in the art.

In another embodiment, it is envisioned to use an inhibitor of a miR-34 family member or an agonist of PNUTS in combination with other therapeutic modalities. For example, use of an inhibitor of a miR-34 family member can be used with an agonist of PNUTS. Also, in addition to the miRNA and PNUTS therapies described above, one may also provide to the subject more "standard" pharmaceutical cardiac therapies. Examples of other therapies include, without limitation, so-called "β-blockers," anti-hypertensives, cardiotonics, anti-thrombotics, vasodilators, hormone antagonists, iontropes, diuretics, endothelin receptor antagonists, calcium channel blockers, phosphodiesterase inhibitors, ACE inhibitors, angiotensin type 2 antagonists and cytokine blockers/inhibitors, and HDAC inhibitors, which are known in the art, such as described in PCT Publication WO 2010/135570, which is incorporated by reference in its entirety.

Combinations may be achieved by contacting cardiac cells with a single composition or a pharmacological formulation that includes one or more inhibitors of a miR-34 family member, one or more agonists of PNUTS, one or more additional cardiac therapies, or any combination thereof. Combinations may also be achieved by contacting the cell with more than one distinct compositions or formulations, at the same time. In one embodiment, one composition includes one or more inhibitors of a miR-34 family member and another composition comprises another cardiac therapy. In another embodiment, one composition includes one or more agonists of PNUTS and another composition comprises another cardiac therapy.

Alternatively, combinations may be administered sequentially. In one embodiment, administration of one or more inhibitors of a miR-34 family member precedes or follows administration of the other cardiac agent(s) by intervals ranging from minutes to weeks. In another embodiment, administration of one or more agonists of PNUTS precedes or follows administration of the other cardiac agent(s) by intervals ranging from minutes to weeks. The other cardiac agent, one or more inhibitors of a miR-34 family member, and/or one or more agonists of PNUTS, can be applied separately to the subject, such that one would generally ensure that a significant period of time did not expire between the time of each delivery, such that the cardiac agent, one or more inhibitors of a miR-34 family member, and/or one or more agonists of PNUTS, would still be able to exert an advantageously combined effect on the cell. In such instances, it is contemplated that one would typically administer the compositions within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either an inhibitor of a miR-34 family member, agonist of PNUTS, or the other cardiac agent will be desired. In this regard, various combinations may be employed. By way of illustration, where "A" is the inhibitor of a miR-34 family member or agonist of PNUTS, and the other cardiac agent is "B," the following permutations based on 3 and 4 total administrations are exemplary:

A/B/A B/A/B B/B/A A/A/B B/A/A A/B/B B/B/B/A B/B/A/B
A/A/B/B A/B/A/B A/B/B/A B/B/A/A B/A/B/A B/A/A/B
   B/B/B/A
A/A/A/B B/A/A/A A/B/A/A A/A/B/A A/B/B/B B/A/B/B
   B/B/A/B

Other combinations are likewise contemplated.

In certain embodiments, the secondary therapeutic agent that can be combined with the inhibitor of a miR-34 family member or agonist of PNUTS may comprise a surgery of some type, which includes, for example, preventative, diagnostic or staging, curative and palliative surgery. Surgery, and in particular a curative surgery, may be used in conjunction with other therapies, such as the miR-34 inhibitors or PNUTS agonists of the present invention and one or more other agents.

Such surgical therapeutic agents for vascular and cardiovascular diseases and disorders are well known to those of skill in the art, and may comprise, but are not limited to, performing surgery on an organism, providing a cardiovascular mechanical prostheses, angioplasty, coronary artery reperfusion, catheter ablation, providing an implantable cardioverter defibrillator to the subject, mechanical circulatory support or a combination thereof. Non-limiting examples of a mechanical circulatory support that may be used in the present invention comprise an intra-aortic balloon counterpulsation, left ventricular assist device or combination thereof.

Colloidal dispersion systems, such as macromolecule complexes, nanocapsules, microspheres, beads, and lipid-based systems including oil-in-water emulsions, micelles, mixed micelles, and liposomes, may be used as delivery vehicles for the oligonucleotide inhibitors of miR-34 function or agonists of PNUTS, or constructs expressing particular miR-34 inhibitors or PNUTS agonists. Commercially available fat emulsions that are suitable for delivering the nucleic acids of the invention to cardiac and skeletal muscle tissues include Intralipid®, Liposyn®, Liposyn® II, Liposyn® III, Nutrilipid, and other similar lipid emulsions. A preferred colloidal system for use as a delivery vehicle in vivo is a liposome (i.e., an artificial membrane vesicle). The preparation and use of such systems is well known in the art. Exemplary formulations are also disclosed in U.S. Pat. No. 5,981,505; U.S. Pat. No. 6,217,900; U.S. Pat. No. 6,383,512; U.S. Pat. No. 5,783,565; U.S. Pat. No. 7,202,227; U.S. Pat. No. 6,379,965; U.S. Pat. No. 6,127,170; U.S. Pat. No. 5,837,533; U.S. Pat. No. 6,747,014; and WO03/093449, which are herein incorporated by reference in their entireties.

One will generally desire to employ appropriate salts and buffers to render delivery vehicles stable and allow for uptake by target cells. Aqueous compositions of the present invention comprise an effective amount of the delivery vehicle comprising the inhibitor polynucleotides (e.g. liposomes or other complexes or expression vectors) dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or polynucleotides of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection, or by direct injection into cardiac tissue. Pharmaceutical compositions comprising a miR-34 inhibitor, PNUTS agonist or expression construct comprising a miRNA inhibitor or PNUTS agonist may also be administered by catheter systems or systems that isolate coronary circulation for delivering therapeutic agents to the heart. Various catheter systems for delivering therapeutic agents to the heart and coronary vasculature are known in the art. Some non-limiting examples of catheter-based delivery methods or coronary isolation methods suitable for use in the present invention are disclosed in U.S. Pat. No. 6,416,510; U.S. Pat. No. 6,716,196; U.S. Pat. No. 6,953,466, WO 2005/082440, WO 2006/089340, U.S. Patent Publication No. 2007/0203445, U.S. Patent Publication No. 2006/0148742, and U.S. Patent Publication No. 2007/0060907, which are all herein incorporated by reference in their entireties. Such compositions would normally be administered as pharmaceutically acceptable compositions as described herein.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids), or from organic acids (e.g., acetic, oxalic, tartaric, mandelic, and the like). Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like).

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

In certain embodiments of the invention, the pharmaceutical compositions of the invention are packaged with or stored within a device for administration. Devices for injectable formulations include, but are not limited to, injection ports, autoinjectors, injection pumps, and injection pens. Devices for aerosolized or powder formulations include, but are not limited to, inhalers, insufflators, aspirators, and the like. Thus, the present invention includes administration devices comprising a pharmaceutical composition of the invention for treating or preventing one or more of the disorders described herein.

This invention is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the invention.

EXAMPLES

Example 1

MiR-34a Expression in Hearts of Aged and Young Mice

To study the physiological aging process, aged mice (18 months old) were compared with young mice (6 weeks old). As expected, hearts of aged mice exhibited increased fibrosis (FIG. 1A), shorter telomeres (FIG. 1B) and increased apoptosis of cardiomyocytes (FIG. 1C). Expression profiling of miRNAs isolated from the hearts of young and aged mice identified a number of dysregulated miRNAs that are known to play a role in cardiac (patho)physiology and in senescence (FIG. 1D, 1E, Table 1).

TABLE 1

| Gene Name | fold | FDR-p |
|---|---|---|
| Upregulated miRNAs | | |
| mmu-miR-574-5p | 2.00 | 0.00001 |
| mmu-miR-29b | 1.98 | 0.00001 |
| mmu-miR-669c | 1.96 | 0.00000 |
| mmu-miR-21 | 1.96 | 0.00001 |
| mmu-miR-34b-5p | 1.80 | 0.00001 |
| mmu-miR-34c | 1.76 | 0.00001 |
| mmu-miR-146a | 1.70 | 0.00002 |
| mmu-miR-468 | 1.63 | 0.00000 |
| mmu-miR-1224 | 1.62 | 0.00031 |
| mmu-miR-142-3p | 1.60 | 0.00174 |
| mmu-miR-24-1* | 1.56 | 0.00040 |
| mmu-miR-221 | 1.56 | 0.00002 |
| mmu-miR-34a | 1.55 | 0.00003 |
| mmu-miR-29a | 1.53 | 0.00011 |
| Downregulated miRNAs | | |
| mmu-miR-181c | −1.61 | 0.00009 |
| mmu-miR-574-5p | −1.58 | 0.00004 |
| mmu-miR-574-5p | −1.53 | 0.00001 |
| mmu-miR-574-5p | −1.51 | 0.00008 |

Figures 1G, 1H, 1I:
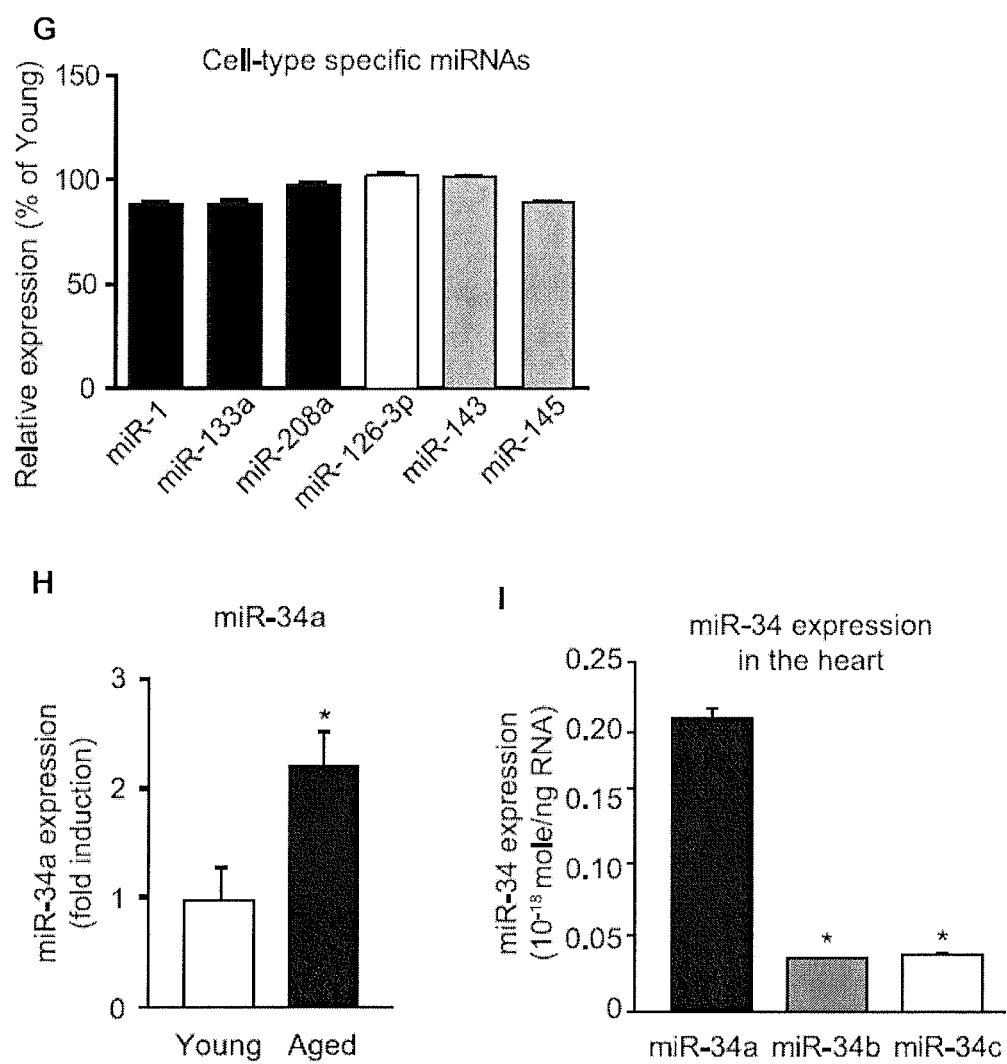
Figure 1J:
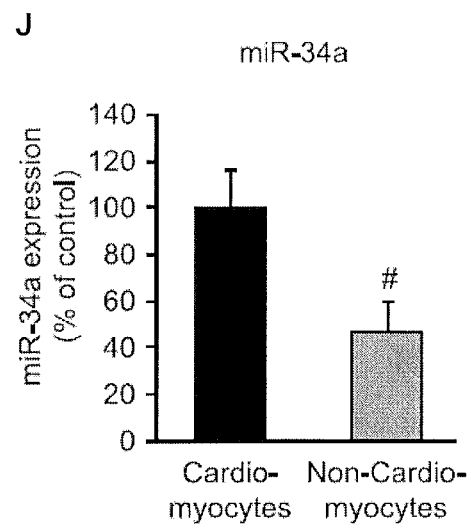
Figure 1K:
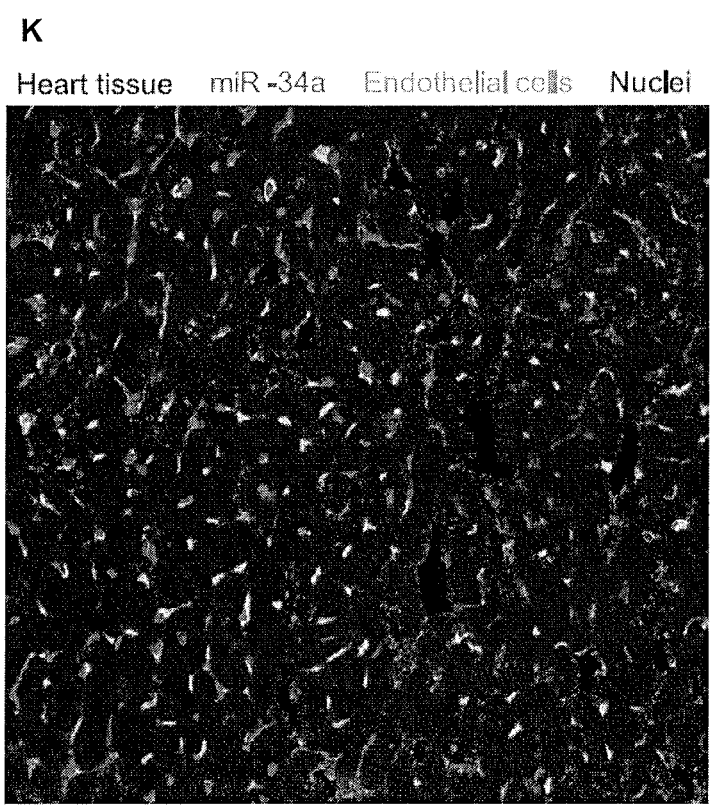

For example, miR-21 and miR-574-5p are known to be induced in the failing heart (6, 7), and miR-146a is known to be induced by senescence (8). Interestingly, the entire miR-34 family (comprising miR-34a, b and c) (FIG. 1F) was significantly upregulated in aged hearts, whereas several cell-type enriched miRNAs such as the endothelial miR-126 (9) and the cardiac myocyte specific miR-208a (10) were unchanged (FIG. 1G). Since miR-34 is known to be involved in apoptosis and senescence (11, 12), this microRNA family was focused on. Quantitative real-time PCR confirmed the age-induced upregulation of miR-34a in the heart (FIG. 1H) and showed that miR-34a is the predominantly expressed miR-34 family member in the heart (FIG. 1I). Moreover, miR-34a levels were ~2-fold higher in isolated cardiomyocytes compared to non-cardiomyocytes (FIG. 1J), indicating that miR-34a is predominantly, but not exclusively, expressed by cardiomyocytes. These data were further corroborated by in situ hybridization for miR-34a on mouse heart sections (FIG. 1K).

Example 2

MiR-34a Inhibition Reduces Cardiomyocyte Apoptosis

Figures 2A, 2B, 2C:
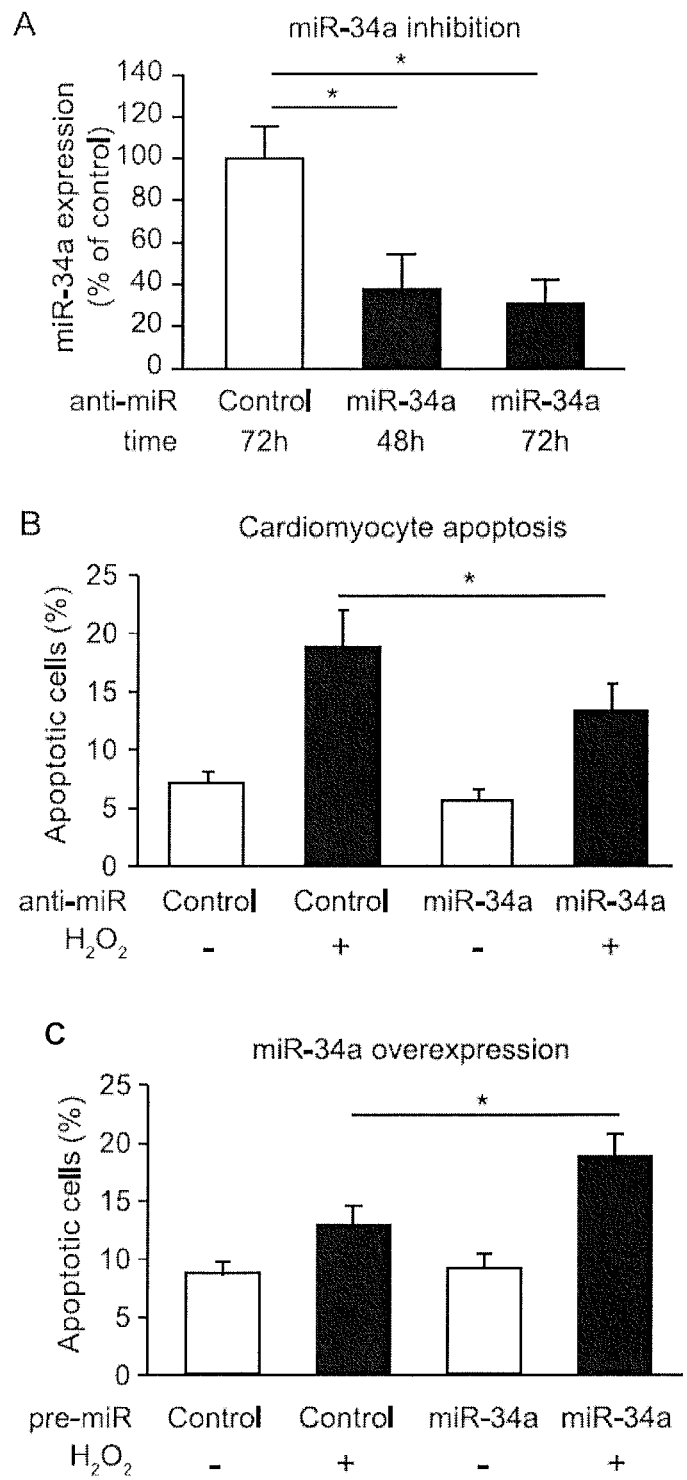
FIG. 2. MiR-34a inhibition reduces cardiomyocyte apoptosis in vitro and in vivo. (A) Primary rat neonatal cardiomyocytes were transfected with anti-sense nucleotides against miR-34a or a non-targeting negative control and miR-34a levels were measured by real-time PCR. (B) Cells were treated with 200 μM hydrogen peroxide 24 h after transfection and apoptosis was measured by flow cytometry at 48 h after transfection; apoptotic cells were identified as Annexin V-positive and 7-AAD-negative cells. (C) MiR-34a overexpression augments hydrogen peroxide-induced apoptosis; primary rat neonatal cardiomyocytes were transfected with pre-miR-34a or nonspecific negative control; these cells were treated with 200 μM hydrogen peroxide 24 h after transfection and apoptosis was measured by flow cytometry at 48 h after transfection; apoptotic cells were identified as Annexin V positive and 7-AAD negative cells (n=7). *p<0.05 (D) Aged mice (18 months old) were treated with 8 mg/kg antagomir-34a (Ant-34a) or scrambled control antagomir (Ant-Control) and miR-34a, b and c expression in the heart was analyzed by real-time PCR after 2 days. (E) Aged mice (18 months old) were treated with antagomir-34a or scrambled control antagomir and cardiomyocyte apoptosis was quantified on histological sections using TUNEL staining by counting apoptotic nuclei of cardiomyocytes. n≥4 for all experiments, *p<0.05.
Figure 2D:
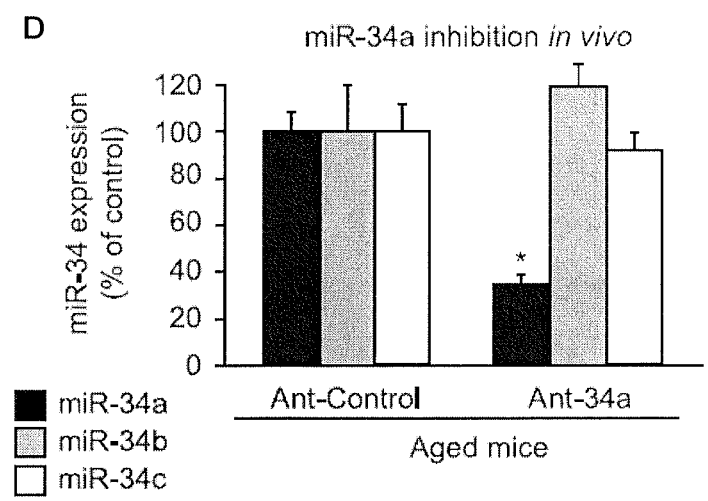
Figure 2E:
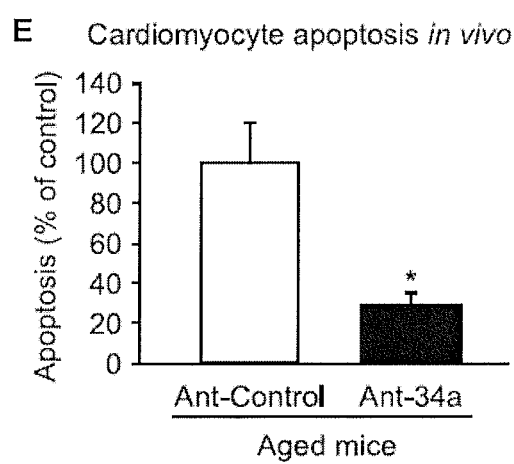

As miR-34a has been shown to induce apoptosis (11) and apoptosis is a classical feature induced by age in the heart (FIG. 1C), the role of miR-34a in cardiomyocyte apoptosis was assessed. Overexpression of a miR-34a inhibitor in rat neonatal cardiomyocytes suppressed miR-34 expression (FIG. 2A) and reduced $H_2O_2$-induced apoptosis (FIG. 2B). In the reverse experiment, pre-miR-34a overexpression significantly augmented $H_2O_2$-induced apoptosis in cardiomyocytes compared to control transfection (FIG. 2C). To study the role of miR-34a in apoptosis in vivo, antisense oligonucleotides, so-called antagomirs (13) were designed. First, antagomir-34a (Ant-34a) was confirmed to specifically reduce the cardiac expression of miR-34a in 18-month old mice ~2.5-fold as compared to scrambled control antagomir (Ant-Control) treated mice, while the related miR-34b and miR-34c were unaffected by Ant-34a treatment (FIG. 2D). Then, to identify whether miR-34a contributes to age-associated apoptosis in the heart, 18-months old mice were treated with 8 mg/kg Ant-34a or Ant-control, the hearts harvested after one week and the apoptotic cells histologically quantified. Ant-34a treatment strikingly reduced the number of apoptotic cells ~3-fold compared to Ant-control treatment (FIG. 2E).

Example 3

Silencing of miR-34a Improves Recovery After Acute Myocardial Infarction

Figures 3A, 3B:
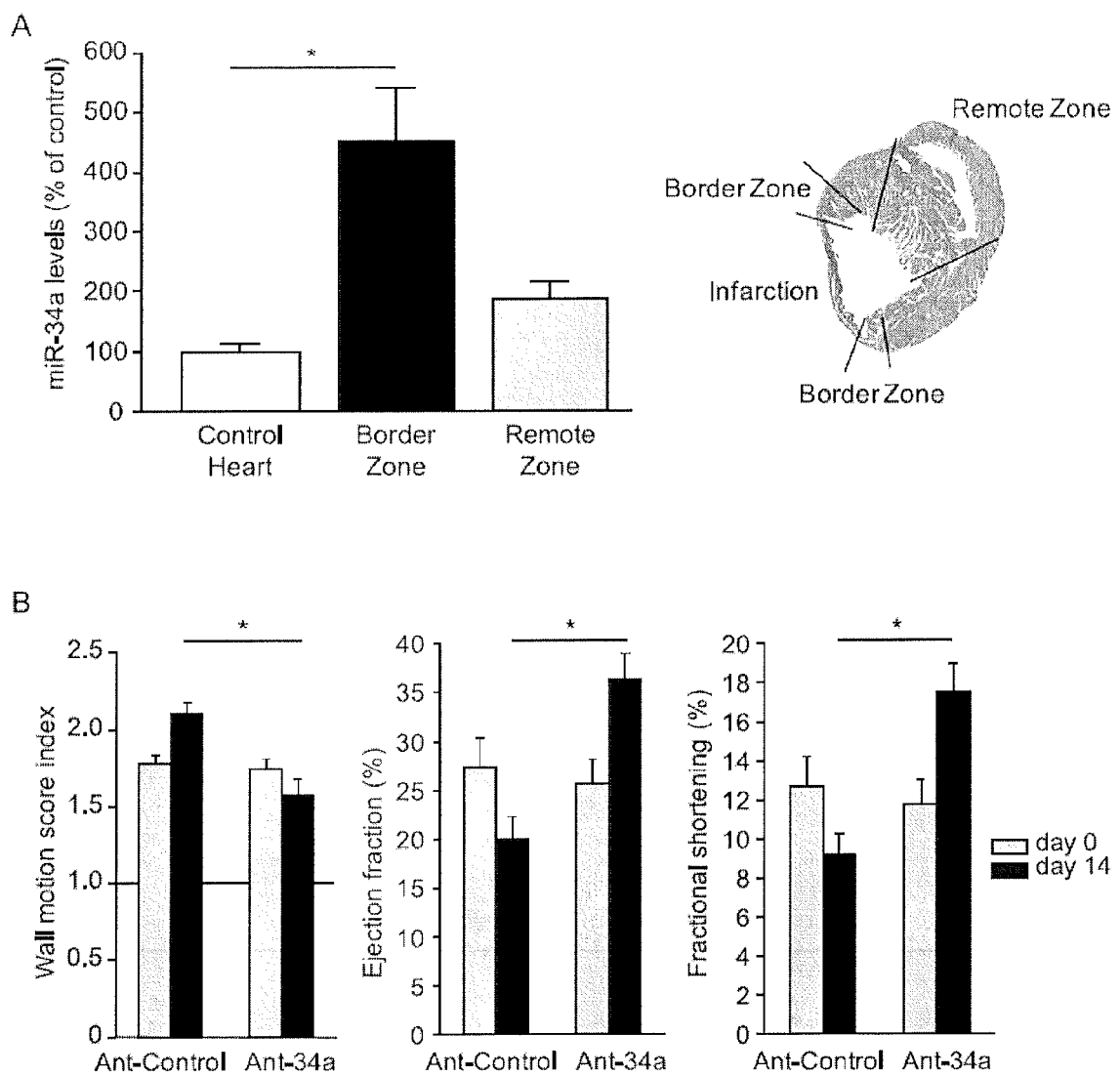
FIG. 3. Silencing of miR-34a improves recovery after acute myocardial infarction. (A) RNA was isolated from the remote zone and the border zone of mice hearts 7 days after an AMI or in hearts of sham-operated control mice (white bar) (n=4 per group); miR-34a levels were measured by real-time PCR. Mice were subjected to AMI, and approximately three hours after the end of the operation, mice were treated with control antagomir or antagomir-34a (Ant-Control, n=12 and Ant-34a, n=14, each 8 mg/kg) and cardiac function was measured by echocardiography. (B) Two days after the AMI, mice received a second antagomir injection and two weeks after the AMI, cardiac function was measured by echocardiography. Echocardiographic data are presented as wall motion score index, ejection fraction and fractional shortening. (C) Histological sections of hearts four weeks after the AMI were analyzed for apoptosis (TUNEL) and fibrosis (Sirius Red staining). *p<0.05 (D, E) miR-34a inhibition reduces AMI-induced apoptosis of both cardiomyocytes and non-cardiomyocytes in vivo; apoptosis in heart tissue of mice that were subjected to an AMI and treated with antagomir-control or antagomir-34a was analyzed using TUNEL and apoptotic (D) cardiomyocytes and (E) non-cardiomyocytes were quantified.
Figures 3C, 3D, 3E:
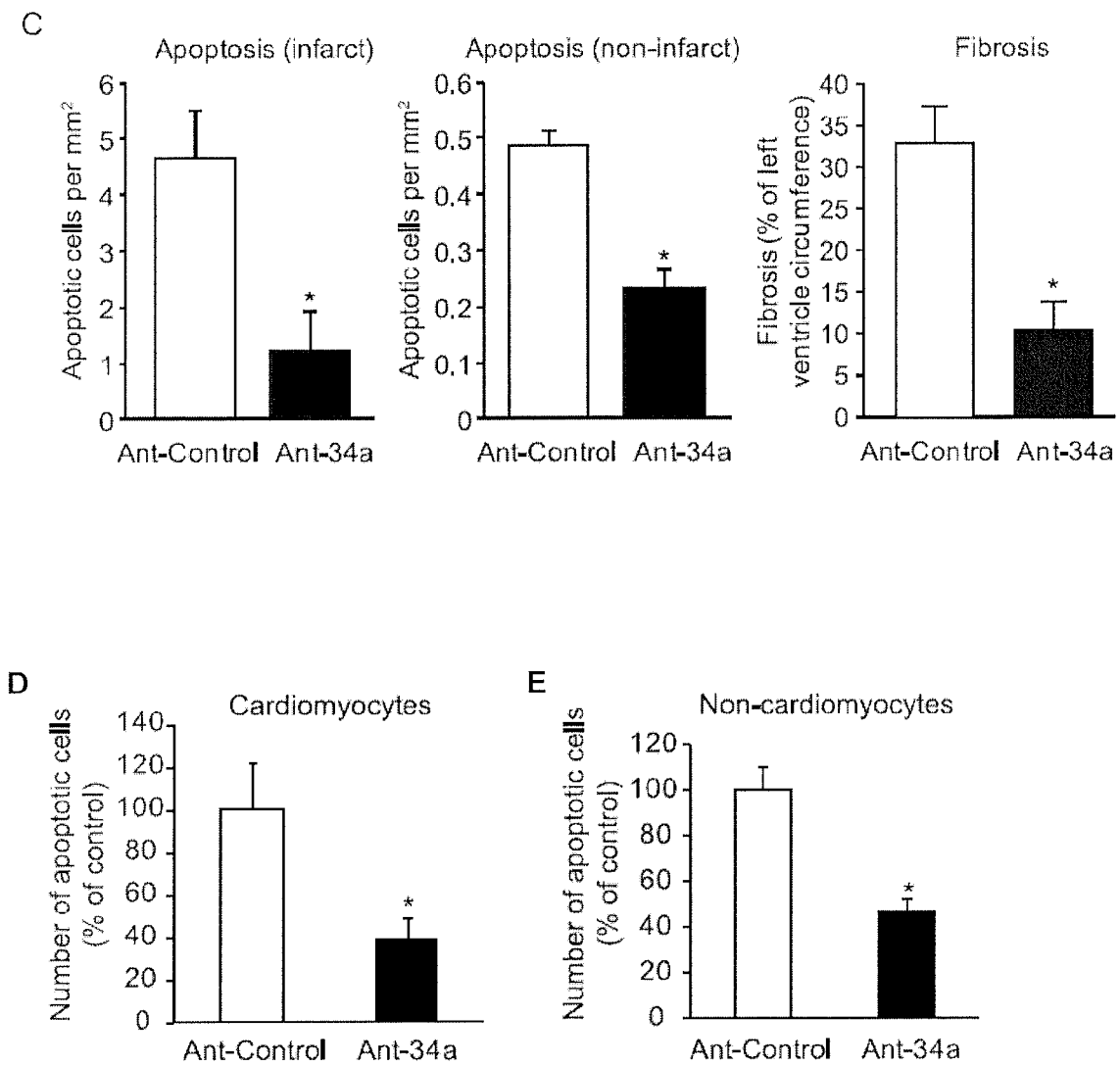

Since apoptosis and fibrosis induced by age are also hallmarks of failing hearts after an acute myocardial infarction (AMI) and age aggravates cardiac dysfunction after AMI, the role of miR-34a in AMI in mice was analyzed. First, miR-34a expression was analyzed in a mouse model of AMI. At 7 days after AMI, miR-34a expression was significantly (4.5-fold) upregulated in the border zone of the myocardial infarction, while miR-34a levels remained unaffected in the remote zone (FIG. 3A). Based on this observation, it was proposed that miR-34a induction after AMI may promote cardiac apoptosis, thereby worsening cardiac function. To test this hypothesis, AMI was induced in mice and Ant-34a or Ant-Control injected intravenously 3-5 hours after the end of surgery and after 2 days. Cardiac function was analyzed by echocardiography directly after inducing AMI and after 14 days, followed by histological analysis of heart sections. The extent of myocardial infarction was similar in the Ant-Control and the Ant-34a-treated groups, as measured by echocardiographic wall motion score index, ejection fraction, and fractional shortening at day 0 (FIG. 3B). Importantly, contractile cardiac function significantly improved in the course of two weeks in Ant-34a-treated mice, whereas heart function further deteriorated in Ant-control-treated mice. These findings were substantiated by analysis of apoptosis and fibrosis on histological sections of the hearts (FIG. 3C). Inhibition of miR-34a reduced the number of apoptotic cells ~4-fold in the infarcted region and ~2-fold in the non-infarcted region. The reduction in the number of apoptotic cells was not confined to cardiomyocytes, but also included non-cardiomyocytes (FIG. 3D, E). Moreover, Ant-34a treatment was associated with a ~2-fold reduction in cardiac fibrosis four weeks after induction of AMI (FIG. 3C, right panel). Together, these results indicate that inhibition of miR-34a improves the restoration of cardiac contractile function after an AMI.

Example 4

MiR-34a Inhibits Neo-Vascularization and Angiogenesis

Figures 4A, 4B, 4C:
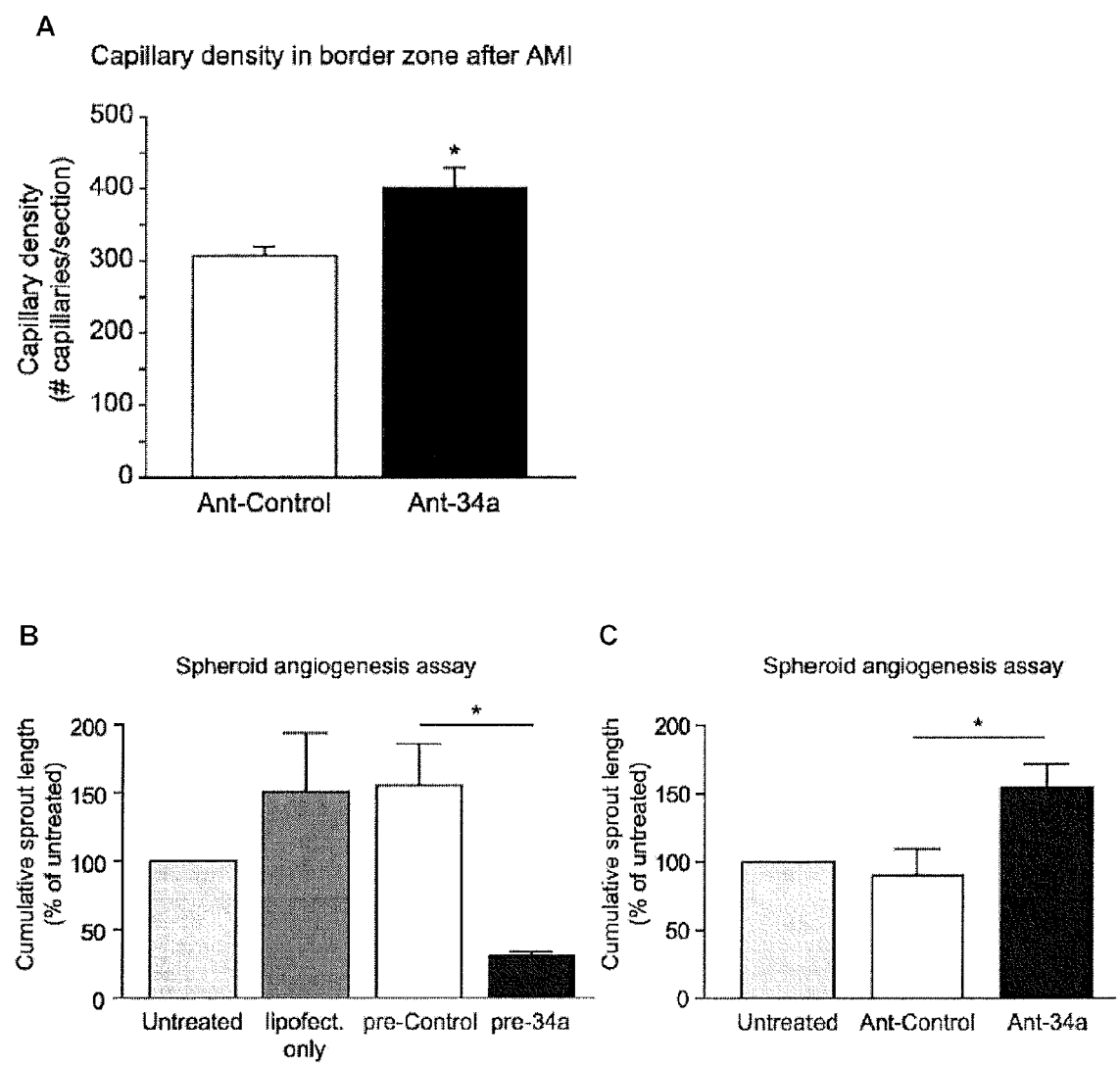
FIG. 4. miR-34a inhibits neo-vascularization after AMI in vivo and angiogenesis in vitro. (A) Four weeks after acute myocardial infarction, mice were sacrificed, heart sections were stained for endothelial cells with Lectin and number of Lectin-positive structures was automatedly quantified. n=6-8, *p<0.05 (B) HUVECs were transfected with transfection reagent only (dark grey bar), a control pre-miR (white bar) or pre-miR-34a (black bar) or left untreated (light grey bar), allowed to sprout in a 3 dimensional spheroid angiogenesis assay and cumulative sprout length was quantified by microscopy. (C) HUVECs were treated with noncoding control antagomirs (white bar), antagomirs targeting miR-34a (black bar) or left untreated (grey bar) and angiogenesis was quantified as in (B). *p<0.05

The results above demonstrated that miR-34a is also expressed in non-cardiomyocytes and miR-34a was previously shown to induce senescence in endothelial cells (14) and to inhibit endothelial progenitor cell functions in vitro (15). Therefore, a potential impact of miR-34a inhibition on neovascularization was investigated. Ant-34a treatment increased capillary density in the border zone of the infarct in vivo (FIG. 4A), and miR-34a controlled angiogenic sprouting in HUVECs in vitro (FIG. 4B, C). These findings indicate that miR-34a inhibition does not only inhibit apoptosis of cardiomyocytes, but also has favorable effects on other cell-types present in the heart, e.g. endothelial cells.

Example 5

Figures 5A, 5B, 5C:
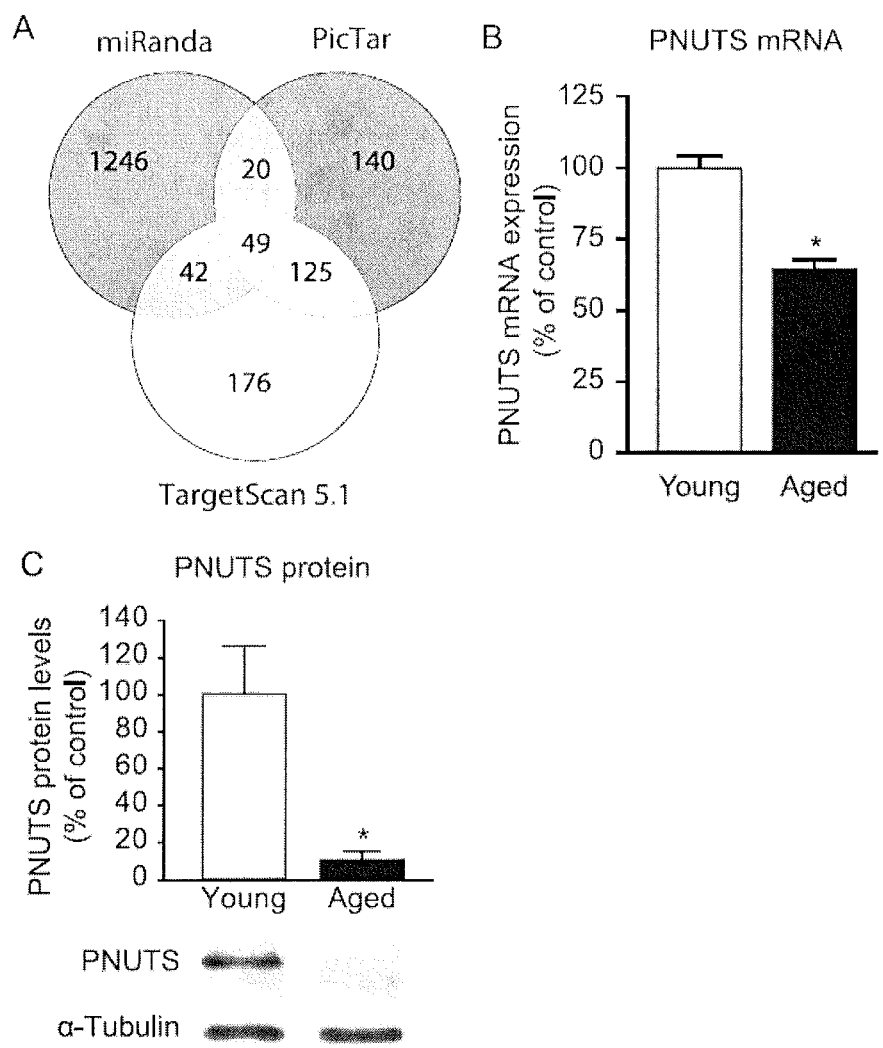
FIG. 5. The novel miR-34a target PNUTS inhibits telomere dysfunction and apoptosis of cardiomyocytes. (A) Three target prediction tools were used to identify targets of miR-34a (miRanda, PicTar and Targetscan 5.1). (B, C) PNUTS (PPP1R10) expression levels from the mRNA microarray profiling (B) of aged vs. young mice hearts and (C) protein levels were measured by Western blot (n=4). (D, E) SIRT1 is post-transcriptionally regulated by age in mouse hearts. (D) Microarray intensities of SIRT1 mRNA in the heart of aged (18 months) and young (6 weeks) mice and (E) cardiac SIRT1 protein levels were analyzed by Western blot. (F) Luciferase constructs containing two copies (or mutations thereof) of the predicted miR-34a target site from the PNUTS 3'UTR were transfected together with pre-miR-34a or scrambled control RNA. After 24 h, luciferase activity was measured and normalized (n=5). (G, H) MiR-34a directly targets PNUTS. (G) Luciferase constructs containing 50 nucleotides (or mutations thereof) surrounding the predicted binding site of miR-34a from the PNUTS 3'UTR in the vector psiCheck2 were transfected together with pre-miR-34a or scrambled control RNA. After 24 h, dual luciferase activity was measured and renilla/firefly luciferase ratios were calculated and normalized. (H) Real-time RT-PCR-based assay using microRNAs as reverse transcriptase primer, adapted from Wang, X., Hu, G., & Zhou, J. Repression of Versican Expression by MicroRNA-143. J. Biol. Chem. 285, 23241-23250 (2010). The x-axis depicts primers that were used for cDNA synthesis and the y-axis depicts the relative expression levels as measured using gene-specific primers for PNUTS (black bars) or housekeeping control RPLPO (PO) (grey bars). (I) Mice were injected with antagomir-34a or control antagomir, which was repeated after three weeks; hearts were harvested 6 weeks after the initial treatment and PNUTS protein levels were measured by Western blot (n=4). (J) Rat neonatal cardiomyocytes were transduced with mock or PNUTS overexpression lentivirus and, after 3 days, transfected with pre-miR-34a or control RNA; apoptosis was stimulated with 200 μM $H_2O_2$ on day 4 and apoptosis was quantified by flow cytometry on day 5 (n=5). (K) Telomere length (n=9) and (L) Chk2 phosphorylation (n=3) was measured in rat neonatal and human cardiomyocytes, respectively, at 6 days after lentiviral transduction with mock (white bar) or PNUTS overexpression lentivirus (black bar). *p<0.05 (M) PNUTS does not affect telomerase activity in rat cardiomyocytes; telomerase activity was measured in rat cardiomyocytes at 6 days after lentiviral transduction with control virus (white bar) or PNUTS overexpression virus (black bar).

Novel MiR-34a Target PNUTS Inhibits Telomere Dysfunction and Apoptosis of Cardiomyocytes To identify putative target mRNAs of miR-34a, three microRNA target prediction tools, miRanda, PicTar and Targetscan 5.1 were used (FIG. 5A). The 49 targets, that were predicted by all three tools (Table 2), were then correlated with aging-mediated downregulated genes (<−1.5-fold) from full-genome mRNA expression profiles of aged and young mice.

TABLE 2

| Symbol | Average Fold | Average Bayes.p |
|---|---|---|
| Ppp1r10 | −1.53 | 0.036 |
| Numbl | −1.30 | 0.164 |
| Dpysl4 | −1.27 | 0.469 |
| Slc30a3 | −1.21 | 0.241 |
| Nrip3 | −1.20 | 0.677 |
| Accn1 | −1.20 | 0.630 |
| Srpr | −1.20 | 0.155 |
| Sidt1 | −1.17 | 0.764 |
| Abr | −1.16 | 0.268 |
| Taf5 | −1.16 | 0.278 |
| Tcfl2 | −1.13 | 0.328 |
| Lef1 | −1.13 | 0.138 |
| Jag1 | −1.13 | 0.448 |
| Crhr1 | −1.11 | 0.785 |
| Pkp4 | −1.09 | 0.172 |
| Foxp1 | −1.07 | 0.440 |
| E2f5 | −1.07 | 0.617 |
| Ptprm | −1.06 | 0.616 |
| Sema4c | −1.06 | 0.546 |
| Dbc1 | −1.05 | 0.939 |
| Galnt7 | −1.04 | 0.619 |
| Ubp1 | −1.03 | 0.707 |
| Cntnap1 | −1.03 | 0.915 |
| Zdhhc23 | −1.01 | 0.980 |
| Strn3 | −1.01 | 0.631 |
| Snx15 | −1.01 | 0.732 |
| Purb | 1.02 | 0.476 |
| Uhrf2 | 1.02 | 0.747 |
| Ppp1r11 | 1.03 | 0.088 |
| Pacs1 | 1.03 | 0.399 |
| Ttc19 | 1.05 | 0.218 |
| Aldoa | 1.06 | 0.108 |

TABLE 2-continued

| Symbol | Average Fold | Average Bayes.p |
|---|---|---|
| Nfe2l1 | 1.08 | 0.258 |
| Mllt3 | 1.08 | 0.477 |
| Eef2k | 1.08 | 0.514 |
| Rras | 1.08 | 0.117 |
| Syvn1 | 1.13 | 0.280 |
| Rps6ka4 | 1.14 | 0.389 |
| Col12a1 | 1.18 | 0.675 |
| Tnrc4 | 1.19 | 0.489 |
| Nav3 | 1.22 | 0.307 |
| Fut8 | 1.22 | 0.350 |
| Plcg1 | 1.26 | 0.536 |
| Btbd11 | 1.34 | 0.401 |
| Phf15 | 1.38 | 0.205 |
| Axl | 1.39 | 0.111 |
| Elmod1 | 1.53 | 0.592 |
| Cacnb3 | 1.82 | 0.009 |
| Myrip | 2.13 | 0.000 |

Figures 5D, 5E, 5F:
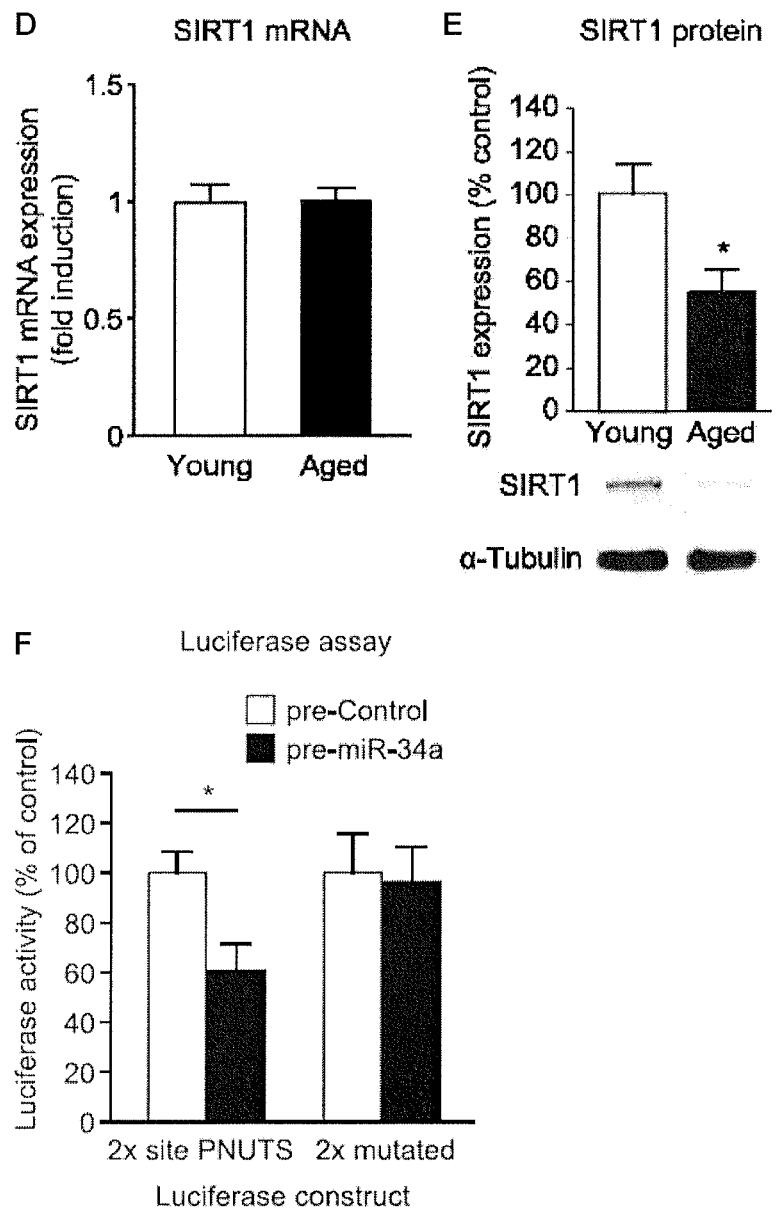

Only one gene was both a predicted target of miR-34a and downregulated by age on the mRNA level, PPP1R10 or PNUTS (FIG. 5B). In line with the putative post-transcriptional mechanisms of action of miRs, PNUTS was even more profoundly downregulated (>10-fold) in aged hearts on the protein level (FIG. 5C), similar to the validated miR-34a target SIRT1 (16) (FIG. 5D, E). PNUTS has been demonstrated to play a role in apoptosis of cancer cell lines (17) and to interact with the telomere regulator TRF2 (5), suggesting a potential role in aging.

Figure 5G:
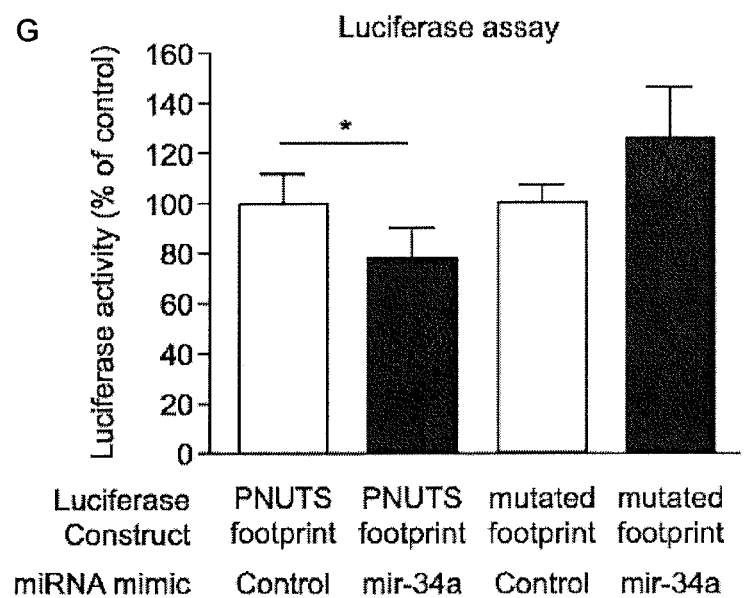
Figure 5H:
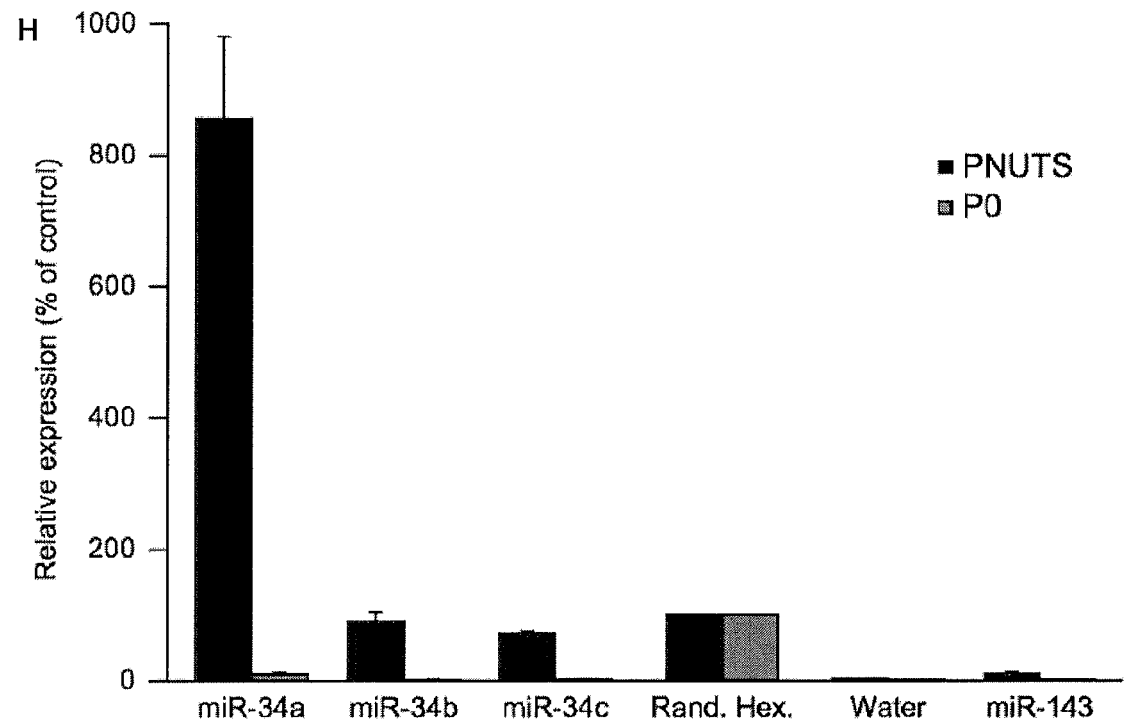
Figure 5I:
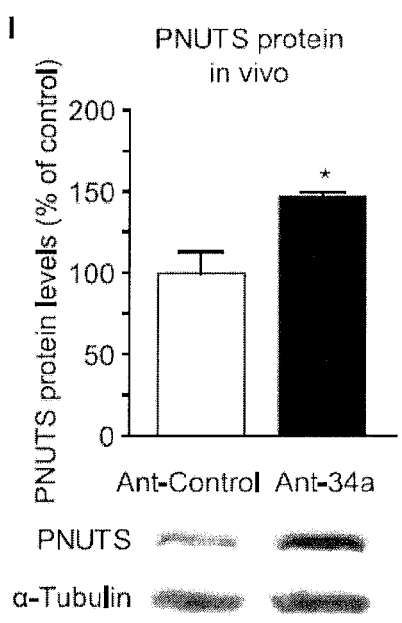

To assess whether PNUTS is a direct target of miR-34a, luciferase reporter constructs were constructed, in which miR-34a target sites of PNUTS were placed in the 3'UTR region. MiR-34a inhibited luciferase activity by ~40%, whereas no effect was observed when the miR-34a target site was mutated, indicating that miR-34a targets the PNUTS 3'UTR (FIG. 5F). A similar approach using 50 nt surrounding the miR-34a seed target sequence from the 3'UTR of PNUTS yielded comparable results and a reverse transcriptase based assay confirmed that miR-34a also binds to the native PNUTS 3'UTR in vitro (FIG. 5G, H). To confirm that miR-34a regulates the expression of PNUTS in the heart in vivo, mice were treated with Ant-Control and Ant-34a and isolated protein from the hearts followed by Western blot analysis for PNUTS. Inhibition of miR-34a profoundly upregulated PNUTS in the heart (FIG. 5I). Together, these results demonstrate that miR-34a directly targets PNUTS.

Figure 5J:
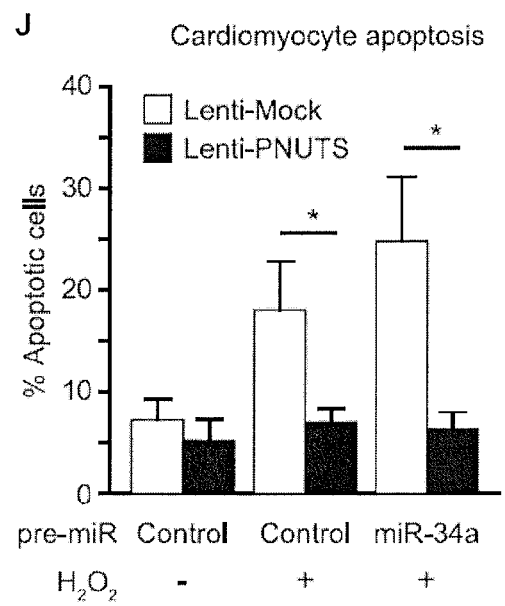
Figures 5K, 5L, 5M:
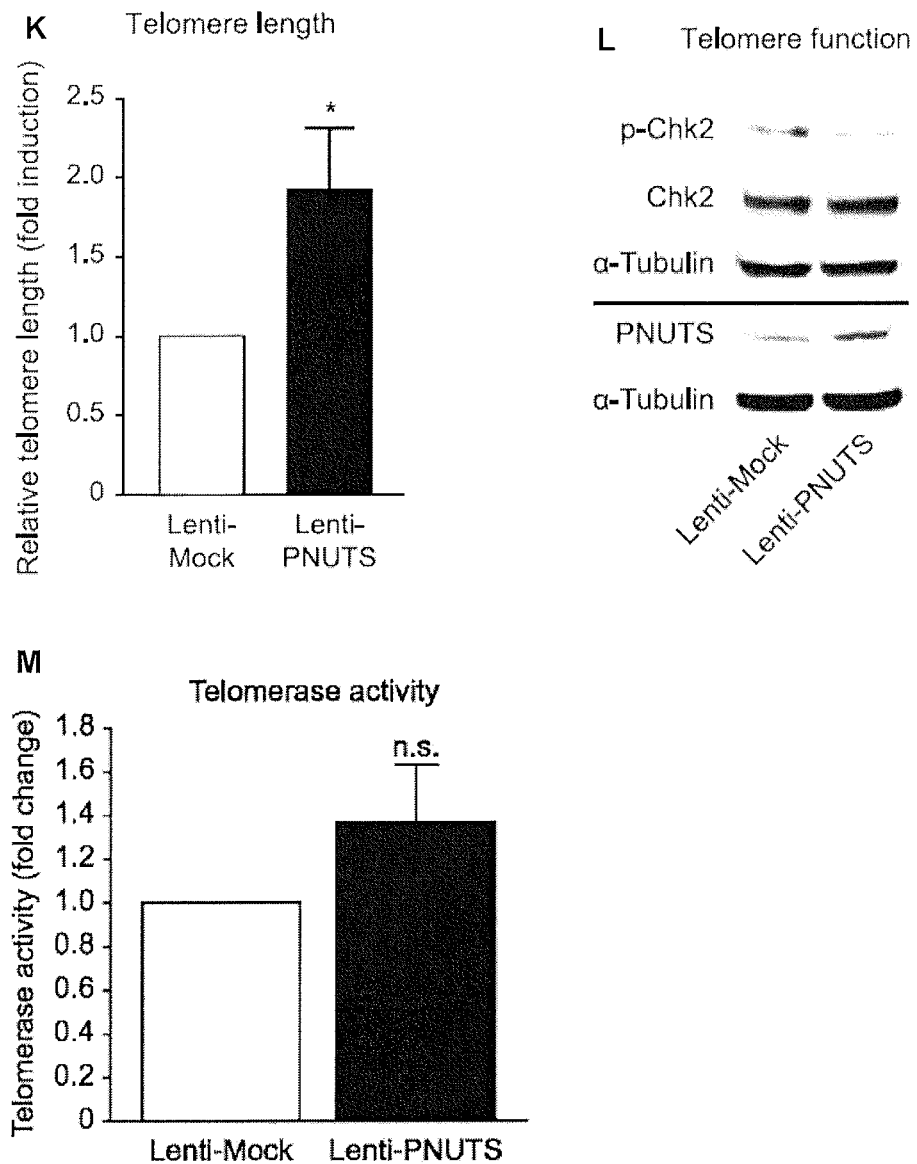

Then, to determine whether PNUTS can inhibit apoptosis in cardiomyocytes, rat cardiomyocytes were transduced either with lentivirus to overexpress human PNUTS or with a mock lentivirus. In PNUTS-overexpressing cells, $H_2O_2$-induced apoptosis was significantly lower and the miR-34a-mediated enhancement of apoptosis was completely abrogated (FIG. 5J). PNUTS is known to interact with the telomere capping protein TRF2, which protects telomeres from degradation by the DNA damage response machinery (18), and telomere erosion can cause age-induced apoptosis and cardiomyocyte apoptosis in heart failure (19). To assess whether inhibition of telomere erosion could be a possible mechanism for the anti-apoptotic effects of PNUTS, telomere length in PNUTS- and mock-transduced cardiomyocytes were measured. PNUTS overexpression resulted in maintained telomere length in rat cardiomyocytes (FIG. 5K). However, telomerase activity was not affected (FIG. 5M), suggesting that PNUTS inhibits telomere shortening rather than induces telomere extension. Furthermore, PNUTS overexpression in human cardiomyocytes repressed phosphorylation of the DNA damage kinase Chk2 (FIG. 5L), which is known to be activated by telomere dysfunction in human heart failure (19), indicating that PNUTS reduces telomere dysfunction-associated signaling.

Figure 6:
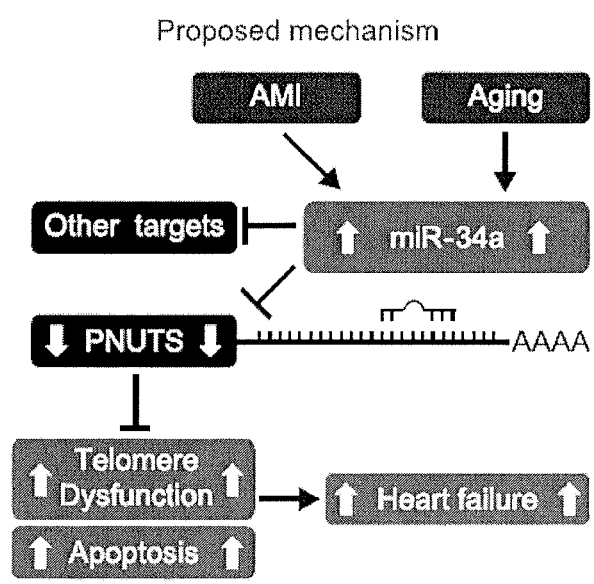

In conclusion, the data shows that inhibition of miR-34a reduces age-induced cardiac apoptosis in vivo, miR-34a is induced after induction of AMI and inhibition of miR-34a enhances cardiac contractile recovery after AMI. Mechanistically, miR-34a regulates the expression of PNUTS, which inhibits telomere erosion and apoptosis, thus providing an explanation for the pro-apoptotic effects of miR-34a in cardiomyocytes (FIG. 6). The finding that PNUTS is reduced in aging and induces telomere maintenance provides a mechanism for the long known paradigm that, even in terminally differentiated cells, telomeres erode during aging.

Thus, the data shows the surprising discovery that the miR-34 family is upregulated in hearts of aged mice and inhibition of miR-34a in 18 month-old mice using specific antagomirs (Ant-34a) reduced apoptosis in the heart. Furthermore, miR-34a is induced after acute myocardial infarction (AMI) in mice and subsequent silencing of miR-34a improves contractile recovery and reduces apoptosis and fibrosis. A novel miR-34a target PNUTS has also been discovered, and found to be strongly downregulated in aged hearts and regulates telomere maintenance and apoptosis in cardiomyocytes. Together, these results indicate that silencing of miR-34a reverses the effects of aging on the heart and improves cardiac function after AMI.

REFERENCES

1. E. G. Lakatta, Age-associated cardiovascular changes in health: impact on cardiovascular disease in older persons *Heart Fail. Rev.* 7, 29 (2002).
2. G. A. Wellenius, M. A. Mittleman, Disparities in myocardial infarction case fatality rates among the elderly: The 20-year Medicare experience *American Heart Journal* 156, 483 (2008).
3. K. R. Cordes, D. Srivastava, MicroRNA Regulation of Cardiovascular Development *Circ Res* 104, 724 (2009).
4. E. van Rooij, W. S. Marshall, E. N. Olson, Toward MicroRNA-Based Therapeutics for Heart Disease: The Sense in Antisense *Circ Res* 103, 919 (2008).
5. H. Kim et al., TRF2 functions as a protein hub and regulates telomere maintenance by recognizing specific peptide motifs *Nat Struct Mol Biol* 16, 372 (2009).
6. T. Thum et al., MicroRNA-21 contributes to myocardial disease by stimulating MAP kinase signalling in fibroblasts *Nature* 456, 980 (2008).
7. E. van Rooij et al., Dysregulation of microRNAs after myocardial infarction reveals a role of miR-29 in cardiac fibrosis *PNAS* 105, 13027 (2008).
8. N. R. Christoffersen et al., p53-independent upregulation of miR-34a during oncogene-induced senescence represses MYC *Cell Death Differ* 17, 236 (2009).
9. A. Kuehbacher, C. Urbich, A. M. Zeiher, S. Dimmeler, Role of Dicer and Drosha for Endothelial MicroRNA Expression and Angiogenesis *Circ Res* 101, 59 (2007).
10. E. van Rooij et al., A Family of microRNAs Encoded by Myosin Genes Governs Myosin Expression and Muscle Performance *Developmental Cell* 17, 662 (2009).
11. H. Hermeking, The miR-34 family in cancer and apoptosis *Cell Death Differ* 17, 193 (2010).
12. L. He et al., A microRNA component of the p53 tumour suppressor network *Nature* 447, 1130 (2007).
13. J. Krutzfeldt et al., Silencing of microRNAs in vivo with 'antagomirs' *Nature* 438, 685 (2005).

14. T. Ito, S. Yagi, M. Yamakuchi, MicroRNA-34a regulation of endothelial senescence *Biochemical and Biophysical Research Communications* 398, 735 (2010).
15. T. Zhao, J. Li, A. F. Chen, MicroRNA-34a induces endothelial progenitor cell senescence and impedes its angiogenesis via suppressing silent information regulator 1 *Am J Physiol Endocrinol Metab* 299, E110 (2010).
16. M. Yamakuchi, M. Ferlito, C. J. Lowenstein, miR-34a repression of SIRT1 regulates apoptosis *PNAS* 105, 13421 (2008).
17. G. De Leon, T. C. Sherry, N. A. Krucher, Reduced expression of PNUTS leads to activation of Rb-phosphatase and caspase-mediated apoptosis *Cancer Biol Ther.* 7, 833 (2008).
18. J. Karlseder, D. Broccoli, Y. Dai, S. Hardy, T. de Lange, p53- and ATM-Dependent Apoptosis Induced by Telomeres Lacking TRF2 *Science* 283, 1321 (1999).
19. H. Oh et al., Telomere attrition and Chk2 activation in human heart failure *Proc. Natl. Acad. Sci U.S.A* 100, 5378 (2003).

The invention claimed is:

1. A method of treating acute myocardial infarction in a subject in need thereof comprising administering to the subject an inhibitor of a miR-34 family member, wherein the inhibitor of the miR-34 family member is an antisense oligonucleotide having a sequence that is at least partially complementary to a mature miR-34a sequence.

2. The method of claim 1, wherein the miR-34 family member is miR-34a, miR-34b, miR-34c or combinations thereof.

3. The method of claim 1, wherein the antisense oligonucleotide comprises a sequence that is at least partially complementary to a sequence of 5'-UGGCAGUGUCU-UAGCUGGUUGU-3' (SEQ ID NO: 1).

4. The method of claim 1, wherein the antisense oligonucleotide comprises at least one sugar and/or backbone modification.

5. The method of claim 4, wherein the at least one sugar modification is a 2'-O-alkyl modification or a bicyclic sugar nucleoside modification.

6. The method of claim 5, wherein the bicyclic sugar nucleoside modification is a locked nucleic acid.

7. The method of claim 4, wherein the backbone modification is a phosphorothioate linkage.

8. The method of claim 1, wherein the antisense oligonucleotide is about 8 to about 18 nucleotides in length.

9. The method of claim 1, wherein the antisense oligonucleotide is about 12 to about 16 nucleotides in length.

10. The method of claim 1, wherein the inhibitor is administered to the subject by an intravenous or subcutaneous route of administration.

11. The method of claim 1, wherein apoptosis of cardiomyocytes is reduced in the subject following administration of the inhibitor as compared to an untreated subject.

12. The method of claim 1, wherein contractile function is increased in the subject following administration of the inhibitor as compared to an untreated subject.

13. The method of claim 1, wherein the expression of PNUTS is increased in the subject following administration of the inhibitor as compared to an untreated subject.

14. The method of claim 1, wherein the subject is a human.

15. The method of claim 1, wherein the antisense oligonucleotide comprises a sequence that is complementary to a seed region of a mature miR-34a sequence.

16. The method of claim 15, wherein the seed region spans bases 2-8 from a 5' portion of a mature miR-34a sequence.

17. The method of claim 15, wherein the antisense oligonucleotide comprises a sequence that is complementary to the sequence of 5'-GGCAGUG-3'.

\* \* \* \* \*

SEQUENCE LISTING

```
<160> NUMBER OF SEQ ID NOS: 31

<210> SEQ ID NO 1
<211> LENGTH: 22
<212> TYPE: RNA
<213> ORGANISM: Artificial Sequence
<220> FEATURE:
<223> OTHER INFORMATION: antisense oligonucleotide

<400> SEQUENCE: 1
uggcaguguc uuagcugguu gu                                                  22

<210> SEQ ID NO 2
<211> LENGTH: 22
<212> TYPE: RNA
<213> ORGANISM: Homo sapiens

<400> SEQUENCE: 2
caaucagcaa guauacugcc cu                                                  22

<210> SEQ ID NO 3
<211> LENGTH: 110
<212> TYPE: RNA
<213> ORGANISM: Homo sapiens

<400> SEQUENCE: 3
ggccagcugu gaguguuucu uuggcagugu cuuagcuggu uguugugagc aauaguaagg         60
aagcaaucag caaguauacu gcccuagaag ugcugcacgu ugugggccc                    110

<210> SEQ ID NO 4
<211> LENGTH: 23
<212> TYPE: RNA
<213> ORGANISM: Homo sapiens

<400> SEQUENCE: 4
uaggcagugu cauuagcuga uug                                                 23

<210> SEQ ID NO 5
<211> LENGTH: 22
<212> TYPE: RNA
<213> ORGANISM: Homo sapiens

<400> SEQUENCE: 5
caaucagcaa guauacugcc cu                                                  22

<210> SEQ ID NO 6
<211> LENGTH: 84
<212> TYPE: RNA
<213> ORGANISM: Homo sapiens

<400> SEQUENCE: 6
gugcucgguu uguaggcagu gucauuagcu gauuguacug uggugguuac aaucacuaac         60
```

| | |
|---|---|
| uccacugcca ucaaaacaag gcac | 84 |

<210> SEQ ID NO 7
<211> LENGTH: 23
<212> TYPE: RNA
<213> ORGANISM: Homo sapiens

<400> SEQUENCE: 7

| | |
|---|---|
| aggcagugua guuagcugau ugc | 23 |

<210> SEQ ID NO 8
<211> LENGTH: 22
<212> TYPE: RNA
<213> ORGANISM: Homo sapiens

<400> SEQUENCE: 8

| | |
|---|---|
| aaucacuaac cacacggcca gg | 22 |

<210> SEQ ID NO 9
<211> LENGTH: 77
<212> TYPE: RNA
<213> ORGANISM: Homo sapiens

<400> SEQUENCE: 9

| | |
|---|---|
| agucuaguua cuaggcagug uaguuagcug auugcuaaua guaccaauca cuaaccacac | 60 |
| ggccagguaa aaagauu | 77 |

<210> SEQ ID NO 10
<211> LENGTH: 4540
<212> TYPE: DNA
<213> ORGANISM: Homo sapiens

<400> SEQUENCE: 10

| | |
|---|---|
| attctggggt tcgtttagag gtttgaattt tctcggagaa agacaggccg gccacgagga | 60 |
| aaacagaaac aagccgcagc aacatctaag cccttgaaag gatcctgaga gaggggggaa | 120 |
| agggaaaaca gcagccacca gcccaaccac ttgtgtcttc tgccccttcc cacctatctt | 180 |
| gcccacccca ccagcccacg ctgcttggga cttgaaatct gtggccgaag gaccgtcact | 240 |
| acataacttc aaaaataatc aaccaccctc ccttcccaaa ccacccaaat tcactcatcc | 300 |
| agcgtttact ttttgaatc cactcagaac ttttttctgc gaccccctc cctaaatgga | 360 |
| gttgggtggg ggggaaatga atactgagtt ggcctttatt ttttaaaaga cttttgatc | 420 |
| caatgaggcc ccctaaataa ttgagttttg ggtcctggtt ggttgtttta ttttttttcc | 480 |
| tccaaaattt taccccctcc ccctgagcc cgaggtgctg acgtcgcaaa aaaattggat | 540 |
| aaaaccacca tcatgggttc gggtcccata gaccccaaag aacttctcaa gggcctggac | 600 |
| agcttcctta accgagatgg ggaagtcaaa agtgtggatg ggatttccaa gatcttcagt | 660 |
| ttgatgaagg aagcacgaaa gatggtgagt cgatgcactt acttgaacat tctcctgcag | 720 |
| acccgttcac cagaaatatt ggtcaaattt attgacgttg gcggctacaa acttcttaac | 780 |
| aattggctga cgtattcaaa gacaaccaac aacattcccc tcctccagca aattctactg | 840 |
| accctgcagc atctaccgct cactgtagac catctcaagc agaacaacac agctaaactg | 900 |
| gtgaagcagc tgagcaagtc aagtgaggat gaagagctcc ggaaattggc ctcagtcctt | 960 |
| gtcagcgact ggatggctgt catccgctct cagagcagta cccagcctgc tgagaaagat | 1020 |
| aagaagaaac gtaagatga aggaaaaagt cgaactaccc ttcctgagcg accttttgaca | 1080 |
| gaggtgaagg ctgagacccg ggctgaggag gccccagaga agaagggga gaagcccaag | 1140 |

```
tctcttcgca ccacagcacc cagtcatgcc aagttccgtt ccactggact agagctggag    1200
acaccatcct tggtgcctgt gaagaagaat gccagcacag tggtggtttc tgacaagtac    1260
aaccttaaac ccatcccct caaacgtcag agcaacgtag ctgctccagg agatgccact     1320
ccccctgcag agaagaaata caagccactc aacacaacac ctaatgccac caaagagatc    1380
aaagtgaaga tcatcccgcc acagcctatg gagggcctgg gctttctgga tgctcttaat    1440
tcagcccctg ttccaggcat caaaattaag aagaaaaaaa aagtactgtc acctacggct    1500
gccaagccaa gccctttga agggaaaacg agcacagaac caagcacagc caaaccttct    1560
tccccagaac cagcaccacc ttctgaggca atggacgcag accgtccagg caccccggtt    1620
ccccctgttg aagtcccgga gctcatggat acagcctctt tggagccagg agctctggat    1680
gccaagccag tggagagtcc tggagatcct aaccaactga cccggaaagg caggaagagg    1740
aaaagtgtga catggcctga ggaaggcaaa ctgagagaat atttctattt tgaattggat    1800
gaaactgaac gagtaaatgt gaataagatc aaggactttg gtgaggcggc taagcgagag    1860
atactgtcag accgacatgc atttgagaca gcgcggcgtc tgagccatga taacatggag    1920
gagaaggtgc cctgggtgtg ccccggccc ctggttctgc cctcacctct tgtcaccct    1980 ggaagcaata gtcaggagcg atatatccag gctgagcggg agaagggaat ccttcaggag    2040
ctcttcctga caaggagag tcctcatgag cctgatcctg agcctacga gcccataccc    2100 cctaaactca tccccctaga tgaggagtgt tccatggatg agactccgta tgttgagact    2160
ctggaacctg ggggtcagg tggctcacct gatgggggcag gaggctccaa gttgcctcca    2220
gttctggcca atcttatggg aagcatgggt gctggaaagg gccccaagg ccctggagga    2280 ggaggcatta atgtccaaga gatcctcacc tccatcatgg gtagcccaaa cagtcatcct    2340
tcagaggaac tactgaaaca accagactat tcggacaaga tcaagcagat gctggtgcca    2400
catggactcc taggccctgg cccaatagcc aatggtttcc caccagggg tcctgggggc    2460 cccaagggca tgcagcactt tccccctgga cctgggggac ctatgccagg tccccatgga    2520
ggccctggtg ggccagtggg tccacgtctt ctgggtcctc cacccctcc ccggggaggt    2580 gatcccttct gggatggccc gggcgaccct atgcggggtg gcccaatgcg gggggtccca    2640
ggaccaggtc ctggaccata ccatagaggc cgaggtggcc gaggaggaaa cgaacctcct    2700
cctcctcctc ctccattccg aggcgccaga ggaggtcgct ctggaggagg accccccaaat    2760 ggacgagggg gccctggtgg gggcatggtt ggaggtggtg ggcatcgtcc tcacgaaggc    2820
cctggtgggg catgggcaa cagcagtgga catcgtcccc acgaaggccc tggcggtggc    2880
atgggaagtg ggcatcgccc ccatgaaggc cctggtggta catgggtgg gggtggagga    2940 catcgtcccc acgaaggccc tggcggtggc atcagtggtg gcagtggcca tcgtccccat    3000
gaaggccctg gcggaggaat gggtgccggt ggtggacatc gccccacga aggccctggc    3060 ggaagcatgg gtgaagtgg tggacatcgt cccatgaag gcctggaca cgggggggcc    3120 catggccacc ggcctcatga tgtccctggt caccgaggcc atgaccatcg agggccgcca    3180
cctcatgagc accgtggcca tgatggtcct ggccacgggg gaggggcca ccgagggcac    3240 gatgaaggcc acagccatgg aggagacatg tcaaaccgcc ctgtctgccg acatttcatg    3300
atgaagggca actgccgcta tgagaacaac tgtgccttct accacccggg tgtcaatggg    3360 cccccccctgc cctagggacc atttgcctgc cctgttcaca caacccctgt ggactgcagc    3420
ctcgctcttt ccaccctgtt atggcttctg tgaggcccat tttccctttt cccagctga    3480
```

-continued

```
tgaggagccg gcccctcag ttcccacttg cttgggttcc tggggttttt ctgatcactg   3540
gtgcgcattg atgtacatat tttcctccag tctggggagg agagagactg gaaacgttcc   3600
tggactgctg aagaggagac ccagttggct tcacttttg agaagattcg ccctgtaccc   3660
caaacccctt tccagtatta cccttaatgc ttgagaacct aaagctggtt atcctggcga   3720
acaccctac ccttctattg cgggtcccca catgcacaca gaactctgac acaggatcag   3780
ctgcacttaa gaaatcatcc cagctaagtt cattattcct catggggtgg ggagatgctg   3840
aaagggtat tgtatatccc actgcactga gagggctcaa tcagctggat ttgagttctg   3900
gaacacacat catccccacc cctccccag cgtgggctca ccattcttag tcctttctca   3960
agtgggacct tcaactttct gtgaacaccc agtctgcgtc ctgggtctgc taggttcgat   4020
gatggcgaac tcgtatctgc atccggtgca agttttagct ggcagaggtg agaccggtgg   4080
tgctggtctg cctttgccaa ctatagccag tctggagact tgataaaata cttcagtgag   4140
accagcttct catcaacttg ggcccggcgt gctgggcctg aaagtcacac tacatgcact   4200
gcctttggga gtcagctcac tccctgctcc cacctggaac cttgccagcg tgaaggaggc   4260
ttccaggtac ttcaccctgt caaccacctc tgaatcccca ccaggcgcct tcctgggtgg   4320
attcaacaag atgattttgc cctttcccag ttctctcctt cactttggca tcagttgttt   4380
tctatgaaaa cagtggattg gttgggtttt gtgcagggtc ttgggttaga gccaaaatgg   4440
atttgaggat gagtattttt tttttggtt ttgtatattt tgtacattaa taataaacag   4500
tggaaagaga agcagcttaa aaaaaaaaaa aaaaaaaa                             4540
```

<210> SEQ ID NO 11
<211> LENGTH: 940
<212> TYPE: PRT
<213> ORGANISM: Homo sapiens

<400> SEQUENCE: 11

```
Met Gly Ser Gly Pro Ile Asp Pro Lys Glu Leu Leu Lys Gly Leu Asp
1               5                   10                  15

Ser Phe Leu Asn Arg Asp Gly Glu Val Lys Ser Val Asp Gly Ile Ser
            20                  25                  30

Lys Ile Phe Ser Leu Met Lys Glu Ala Arg Lys Met Val Ser Arg Cys
        35                  40                  45

Thr Tyr Leu Asn Ile Leu Leu Gln Thr Arg Ser Pro Glu Ile Leu Val
    50                  55                  60

Lys Phe Ile Asp Val Gly Gly Tyr Lys Leu Leu Asn Asn Trp Leu Thr
65                  70                  75                  80

Tyr Ser Lys Thr Thr Asn Asn Ile Pro Leu Leu Gln Gln Ile Leu Leu
                85                  90                  95

Thr Leu Gln His Leu Pro Leu Thr Val Asp His Leu Lys Gln Asn Asn
            100                 105                 110

Thr Ala Lys Leu Val Lys Gln Leu Ser Lys Ser Ser Glu Asp Glu Glu
        115                 120                 125

Leu Arg Lys Leu Ala Ser Val Leu Val Ser Asp Trp Met Ala Val Ile
    130                 135                 140

Arg Ser Gln Ser Ser Thr Gln Pro Ala Glu Lys Asp Lys Lys Arg
145                 150                 155                 160

Lys Asp Glu Gly Lys Ser Arg Thr Thr Leu Pro Glu Arg Pro Leu Thr
                165                 170                 175

Glu Val Lys Ala Glu Thr Arg Ala Glu Glu Ala Pro Glu Lys Lys Arg
            180                 185                 190
```

```
Glu Lys Pro Lys Ser Leu Arg Thr Thr Ala Pro Ser His Ala Lys Phe
            195                 200                 205

Arg Ser Thr Gly Leu Glu Leu Glu Thr Pro Ser Leu Val Pro Val Lys
            210                 215                 220

Lys Asn Ala Ser Thr Val Val Ser Asp Lys Tyr Asn Leu Lys Pro
225                 230                 235                 240

Ile Pro Leu Lys Arg Gln Ser Asn Val Ala Ala Pro Gly Asp Ala Thr
                245                 250                 255

Pro Pro Ala Glu Lys Lys Tyr Lys Pro Leu Asn Thr Thr Pro Asn Ala
                260                 265                 270

Thr Lys Glu Ile Lys Val Lys Ile Ile Pro Pro Gln Pro Met Glu Gly
            275                 280                 285

Leu Gly Phe Leu Asp Ala Leu Asn Ser Ala Pro Val Pro Gly Ile Lys
            290                 295                 300

Ile Lys Lys Lys Lys Val Leu Ser Pro Thr Ala Ala Lys Pro Ser
305                 310                 315                 320

Pro Phe Glu Gly Lys Thr Ser Thr Glu Pro Ser Thr Ala Lys Pro Ser
                325                 330                 335

Ser Pro Glu Pro Ala Pro Pro Ser Glu Ala Met Asp Ala Asp Arg Pro
            340                 345                 350

Gly Thr Pro Val Pro Pro Val Glu Val Pro Glu Leu Met Asp Thr Ala
            355                 360                 365

Ser Leu Glu Pro Gly Ala Leu Asp Ala Lys Pro Val Glu Ser Pro Gly
            370                 375                 380

Asp Pro Asn Gln Leu Thr Arg Lys Gly Arg Lys Arg Lys Ser Val Thr
385                 390                 395                 400

Trp Pro Glu Glu Gly Lys Leu Arg Glu Tyr Phe Tyr Phe Glu Leu Asp
                405                 410                 415

Glu Thr Glu Arg Val Asn Val Asn Lys Ile Lys Asp Phe Gly Glu Ala
            420                 425                 430

Ala Lys Arg Glu Ile Leu Ser Asp Arg His Ala Phe Glu Thr Ala Arg
            435                 440                 445

Arg Leu Ser His Asp Asn Met Glu Glu Lys Val Pro Trp Val Cys Pro
            450                 455                 460

Arg Pro Leu Val Leu Pro Ser Pro Leu Val Thr Pro Gly Ser Asn Ser
465                 470                 475                 480

Gln Glu Arg Tyr Ile Gln Ala Glu Arg Glu Lys Gly Ile Leu Gln Glu
                485                 490                 495

Leu Phe Leu Asn Lys Glu Ser Pro His Glu Pro Asp Pro Glu Pro Tyr
            500                 505                 510

Glu Pro Ile Pro Pro Lys Leu Ile Pro Leu Asp Glu Glu Cys Ser Met
            515                 520                 525

Asp Glu Thr Pro Tyr Val Glu Thr Leu Glu Pro Gly Gly Ser Gly Gly
            530                 535                 540

Ser Pro Asp Gly Ala Gly Gly Ser Lys Leu Pro Pro Val Leu Ala Asn
545                 550                 555                 560

Leu Met Gly Ser Met Gly Ala Gly Lys Gly Pro Gln Gly Pro Gly Gly
                565                 570                 575

Gly Gly Ile Asn Val Gln Glu Ile Leu Thr Ser Ile Met Gly Ser Pro
            580                 585                 590

Asn Ser His Pro Ser Glu Glu Leu Leu Lys Gln Pro Asp Tyr Ser Asp
            595                 600                 605
```

Lys Ile Lys Gln Met Leu Val Pro His Gly Leu Leu Gly Pro Gly Pro
610                 615                 620

Ile Ala Asn Gly Phe Pro Pro Gly Gly Pro Gly Gly Pro Lys Gly Met
625                 630                 635                 640

Gln His Phe Pro Pro Gly Pro Gly Gly Pro Met Pro Gly Pro His Gly
        645                 650                 655

Gly Pro Gly Gly Pro Val Gly Pro Arg Leu Leu Gly Pro Pro Pro Pro
            660                 665                 670

Pro Arg Gly Gly Asp Pro Phe Trp Asp Gly Pro Gly Asp Pro Met Arg
                675                 680                 685

Gly Gly Pro Met Arg Gly Gly Pro Gly Pro Gly Pro Gly Pro Tyr His
690                 695                 700

Arg Gly Arg Gly Gly Arg Gly Asn Glu Pro Pro Pro Pro Pro
705                 710                 715                 720

Pro Phe Arg Gly Ala Arg Gly Gly Arg Ser Gly Gly Pro Asn
                725                 730                 735

Gly Arg Gly Gly Pro Gly Gly Met Val Gly Gly Gly His Arg
            740                 745                 750

Pro His Glu Gly Pro Gly Gly Met Gly Asn Ser Ser Gly His Arg
    755                 760                 765

Pro His Glu Gly Pro Gly Gly Met Gly Ser Gly His Arg Pro His
    770                 775                 780

Glu Gly Pro Gly Gly Ser Met Gly Gly Gly His Arg Pro His
785                 790                 795                 800

Glu Gly Pro Gly Gly Gly Ile Ser Gly Gly Ser Gly His Arg Pro His
                805                 810                 815

Glu Gly Pro Gly Gly Gly Met Gly Ala Gly Gly His Arg Pro His
                820                 825                 830

Glu Gly Pro Gly Gly Ser Met Gly Gly Ser Gly His Arg Pro His
            835                 840                 845

Glu Gly Pro Gly His Gly Gly Pro His Gly His Arg Pro His Asp Val
    850                 855                 860

Pro Gly His Arg Gly His Asp His Arg Gly Pro Pro His Glu His
865                 870                 875                 880

Arg Gly His Asp Gly Pro Gly His Gly Gly His Arg Gly His
                885                 890                 895

Asp Gly Gly His Ser His Gly Gly Asp Met Ser Asn Arg Pro Val Cys
        900                 905                 910

Arg His Phe Met Met Lys Gly Asn Cys Arg Tyr Glu Asn Asn Cys Ala
            915                 920                 925

Phe Tyr His Pro Gly Val Asn Gly Pro Pro Leu Pro
930                 935                 940

<210> SEQ ID NO 12
<211> LENGTH: 22
<212> TYPE: RNA
<213> ORGANISM: Artificial Sequence
<220> FEATURE:
<223> OTHER INFORMATION: antisense oligonucleotide

<400> SEQUENCE: 12
acaaccagcu aagacacugc ca                                          22

<210> SEQ ID NO 13
<211> LENGTH: 8
<212> TYPE: RNA

```
<213> ORGANISM: Artificial Sequence
<220> FEATURE:
<223> OTHER INFORMATION: antisense oligonucleotide

<400> SEQUENCE: 13 cacugcca                                                                      8

<210> SEQ ID NO 14
<211> LENGTH: 8
<212> TYPE: RNA
<213> ORGANISM: Artificial Sequence
<220> FEATURE:
<223> OTHER INFORMATION: antisense oligonucleotide

<400> SEQUENCE: 14 acacugcc                                                                      8

<210> SEQ ID NO 15
<211> LENGTH: 10
<212> TYPE: RNA
<213> ORGANISM: Artificial Sequence
<220> FEATURE:
<223> OTHER INFORMATION: antisense oligonucleotide

<400> SEQUENCE: 15
gacacugcca                                                                   10

<210> SEQ ID NO 16
<211> LENGTH: 12
<212> TYPE: RNA
<213> ORGANISM: Artificial Sequence
<220> FEATURE:
<223> OTHER INFORMATION: antisense oligonucleotide

<400> SEQUENCE: 16
aagacacugc ca                                                                12

<210> SEQ ID NO 17
<211> LENGTH: 14
<212> TYPE: RNA
<213> ORGANISM: Artificial Sequence
<220> FEATURE:
<223> OTHER INFORMATION: antisense oligonucleotide

<400> SEQUENCE: 17
cuaagacacu gcca                                                              14

<210> SEQ ID NO 18
<211> LENGTH: 16
<212> TYPE: RNA
<213> ORGANISM: Artificial Sequence
<220> FEATURE:
<223> OTHER INFORMATION: antisense oligonucleotide

<400> SEQUENCE: 18
agcuaagaca cugcca                                                            16

<210> SEQ ID NO 19
<211> LENGTH: 16
<212> TYPE: RNA
<213> ORGANISM: Artificial Sequence
<220> FEATURE:
<223> OTHER INFORMATION: antisense oligonucleotide

<400> SEQUENCE: 19
cagcuaagac acugcc                                                            16
```

-continued

```
<210> SEQ ID NO 20
<211> LENGTH: 18
<212> TYPE: RNA
<213> ORGANISM: Artificial Sequence
<220> FEATURE:
<223> OTHER INFORMATION: antisense oligonucleotide

<400> SEQUENCE: 20
ccagcuaaga cacugcca                                                       18

<210> SEQ ID NO 21
<211> LENGTH: 15
<212> TYPE: RNA
<213> ORGANISM: Artificial Sequence
<220> FEATURE:
<223> OTHER INFORMATION: antisense oligonucleotide

<400> SEQUENCE: 21
agcuaagaca cugcc                                                          15

<210> SEQ ID NO 22
<211> LENGTH: 22
<212> TYPE: RNA
<213> ORGANISM: Artificial Sequence
<220> FEATURE:
<223> OTHER INFORMATION: antisense oligonucleotide

<400> SEQUENCE: 22
agggcaguau acuugcugau ug                                                  22

<210> SEQ ID NO 23
<211> LENGTH: 8
<212> TYPE: RNA
<213> ORGANISM: Artificial Sequence
<220> FEATURE:
<223> OTHER INFORMATION: antisense oligonucleotide

<400> SEQUENCE: 23 gcugauug                                                                   8

<210> SEQ ID NO 24
<211> LENGTH: 8
<212> TYPE: RNA
<213> ORGANISM: Artificial Sequence
<220> FEATURE:
<223> OTHER INFORMATION: antisense oligonucleotide

<400> SEQUENCE: 24 ugcugauu                                                                   8

<210> SEQ ID NO 25
<211> LENGTH: 10
<212> TYPE: RNA
<213> ORGANISM: Artificial Sequence
<220> FEATURE:
<223> OTHER INFORMATION: antisense oligonucleotide

<400> SEQUENCE: 25
uugcugauug                                                                10

<210> SEQ ID NO 26
<211> LENGTH: 12
<212> TYPE: RNA
<213> ORGANISM: Artificial Sequence
<220> FEATURE:
```

```
<223> OTHER INFORMATION: antisense oligonucleotide

<400> SEQUENCE: 26
acuugcugau ug                                                              12

<210> SEQ ID NO 27
<211> LENGTH: 14
<212> TYPE: RNA
<213> ORGANISM: Artificial Sequence
<220> FEATURE:
<223> OTHER INFORMATION: antisense oligonucleotide

<400> SEQUENCE: 27
auacuugcug auug                                                            14

<210> SEQ ID NO 28
<211> LENGTH: 16
<212> TYPE: RNA
<213> ORGANISM: Artificial Sequence
<220> FEATURE:
<223> OTHER INFORMATION: antisense oligonucleotide

<400> SEQUENCE: 28
guauacuugc ugauug                                                          16

<210> SEQ ID NO 29
<211> LENGTH: 16
<212> TYPE: RNA
<213> ORGANISM: Artificial Sequence
<220> FEATURE:
<223> OTHER INFORMATION: antisense oligonucleotide

<400> SEQUENCE: 29
aguauacuug cugauu                                                          16

<210> SEQ ID NO 30
<211> LENGTH: 18
<212> TYPE: RNA
<213> ORGANISM: Artificial Sequence
<220> FEATURE:
<223> OTHER INFORMATION: antisense oligonucleotide

<400> SEQUENCE: 30
caguauacuu gcugauug                                                        18

<210> SEQ ID NO 31
<211> LENGTH: 15
<212> TYPE: RNA
<213> ORGANISM: Artificial Sequence
<220> FEATURE:
<223> OTHER INFORMATION: antisense oligonucleotide

<400> SEQUENCE: 31
guauacuugc ugauu                                                           15
```